United States Patent
Wigler et al.

(10) Patent No.: US 10,731,149 B2
(45) Date of Patent: Aug. 4, 2020

(54) GENETIC COPY NUMBER DETERMINATION USING HIGH THROUGHPUT MULTIPLEX SEQUENCING OF SMASHED NUCLEOTIDES

(71) Applicants: Michael H. Wigler, Lloyd Harbor, NY (US); Dan Levy, Merrick, NY (US); Zihua Wang, East Northport, NY (US)

(72) Inventors: Michael H. Wigler, Lloyd Harbor, NY (US); Dan Levy, Merrick, NY (US); Zihua Wang, East Northport, NY (US)

(73) Assignee: Cold Spring Harbor Laboratory, Cold Spring Harbor, NY (US)

( * ) Notice: Subject to any disclaimer, the term of this patent is extended or adjusted under 35 U.S.C. 154(b) by 0 days.

(21) Appl. No.: 15/419,878

(22) Filed: Jan. 30, 2017

(65) Prior Publication Data
US 2017/0152548 A1   Jun. 1, 2017

Related U.S. Application Data

(63) Continuation of application No. PCT/US2016/050750, filed on Sep. 8, 2016.
(Continued)

(51) Int. Cl.
C12N 15/10 (2006.01)
C12Q 1/68 (2018.01)
(Continued)

(52) U.S. Cl.
CPC ..... *C12N 15/1065* (2013.01); *C12N 15/1093* (2013.01); *C12Q 1/68* (2013.01);
(Continued)

(58) Field of Classification Search
CPC .. C12N 15/1065; C12N 15/1093; C12Q 1/68; C12Q 1/6806; C12Q 1/6809;
(Continued)

(56) References Cited

U.S. PATENT DOCUMENTS

| 5,830,721 A | 11/1998 | Stemmer et al. |
| 6,383,743 B1 | 5/2002 | Kinzler et al. |

(Continued)

FOREIGN PATENT DOCUMENTS

| CN | 103374518 | 10/2013 |
| CN | 103725773 | 11/2015 |

(Continued)

OTHER PUBLICATIONS

Myllykangas et al. (2011) "Overview of Sequencing Technology Platforms" in Bioinformatics for High Throughput Sequencing, eds Rodriguez-Ezpeleta, Naiara, Hackenberg, Michael, Aransay, Ana M., Springer New York, pp. 11-25.*
(Continued)

*Primary Examiner* — Jeremy C Flinders
(74) *Attorney, Agent, or Firm* — Gary J. Gershik; Cooper & Dunham LLP

(57) ABSTRACT

The present invention, SMASH (Short Multiply Aggregated Sequence Homologies), is a technique designed to pack multiple independent mappings into every read. Specifically, the invention relates to a composition comprising a first mixture of different chimeric genomic nucleic acid fragments, wherein each different fragment in the mixture comprises randomly ligated DNA segments, wherein each DNA segment in the fragment is a nucleic acid molecule at least 27 base pairs in length resulting from random fragmentation of a single genome. The invention also relates to methods for generating said composition and use of said composition to obtain genomic information, for example, copy number variation.

13 Claims, 9 Drawing Sheets
Specification includes a Sequence Listing.

Related U.S. Application Data

(60) Provisional application No. 62/215,540, filed on Sep. 8, 2015, provisional application No. 62/250,405, filed on Nov. 3, 2015, provisional application No. 62/292,151, filed on Feb. 5, 2016.

(51) Int. Cl.

| | | |
|---|---|---|
| *C40B 40/06* | (2006.01) | |
| *C12Q 1/6806* | (2018.01) | |
| *C12Q 1/6809* | (2018.01) | |
| *C12Q 1/6855* | (2018.01) | |
| *G16B 30/00* | (2019.01) | |

(52) U.S. Cl.
CPC ......... *C12Q 1/6806* (2013.01); *C12Q 1/6809* (2013.01); *C12Q 1/6855* (2013.01); *C40B 40/06* (2013.01); *G16B 30/00* (2019.02); *C12Q 2535/122* (2013.01)

(58) Field of Classification Search
CPC ............ C12Q 1/6855; C12Q 2535/122; C40B 40/06; G16B 30/00
See application file for complete search history.

(56) References Cited

U.S. PATENT DOCUMENTS

| | | | |
|---|---|---|---|
| 6,498,013 | B1 | 12/2002 | Velculescu et al. |
| 7,932,029 | B1 | 4/2011 | Lok |
| 8,428,882 | B2 | 4/2013 | Chiu et al. |
| 8,722,368 | B2 | 5/2014 | Casbon et al. |
| 2005/0260655 | A1 | 11/2005 | Liu et al. |
| 2006/0228714 | A1* | 10/2006 | Meyerson .......... C12N 15/1093 435/6.14 |
| 2009/0137402 | A1 | 5/2009 | Wang et al. |
| 2013/0203605 | A1 | 8/2013 | Shendure et al. |
| 2013/0231253 | A1 | 9/2013 | Amorese et al. |
| 2013/0316911 | A1 | 11/2013 | Scherer et al. |
| 2014/0031240 | A1 | 1/2014 | Behlke et al. |
| 2014/0141981 | A1 | 5/2014 | Zimmermann et al. |
| 2014/0155271 | A1 | 6/2014 | Hatchwell et al. |
| 2014/0162894 | A1 | 6/2014 | Hatchwell et al. |
| 2014/0195164 | A1 | 7/2014 | Lo et al. |
| 2014/0342354 | A1 | 11/2014 | Evans et al. |
| 2015/0118685 | A1 | 4/2015 | Clark et al. |
| 2015/0133317 | A1 | 5/2015 | Robinson et al. |
| 2015/0167068 | A1 | 6/2015 | Lagace et al. |
| 2015/0211070 | A1 | 7/2015 | Seligson et al. |
| 2015/0265995 | A1 | 9/2015 | Head et al. |
| 2015/0286773 | A1 | 10/2015 | Talkowski et al. |
| 2015/0307947 | A1 | 10/2015 | Basu et al. |
| 2015/0344873 | A1 | 12/2015 | Xiao et al. |
| 2015/0344938 | A1 | 12/2015 | Bramlett et al. |
| 2015/0379192 | A9 | 12/2015 | Drmanac et al. |
| 2016/0108394 | A1 | 4/2016 | Lok et al. |
| 2016/0019338 | A1 | 8/2016 | Chudova et al. |

FOREIGN PATENT DOCUMENTS

| | | |
|---|---|---|
| EP | 3067807 | 9/2016 |
| WO | WO 2001/029211 | 4/2001 |
| WO | WO 2002/006469 | 1/2002 |
| WO | WO 2010/093465 | 8/2010 |
| WO | WO 2012/054873 A2 | 4/2012 |
| WO | WO 2012/141712 | 10/2012 |
| WO | WO 2013/015793 | 1/2013 |
| WO | WO 2014/149134 A2 | 9/2014 |
| WO | WO 2014/197805 | 2/2015 |
| WO | WO 2015/017527 | 2/2015 |
| WO | WO 2015/089333 | 6/2015 |
| WO | WO 2015/118077 | 8/2015 |

OTHER PUBLICATIONS

Craig et al. (2008) "Identification of genetic variants using bar-coded multiplexed sequencing" Nature Methods 5(10):887-893 including Supplementary Methods.*
NEB Enzyme Finder, 4 bases sequences, obtained Oct. 4, 2017, https://www.neb.com/tools-and-resources/interactive-tools/enzyme-finder?searchType=12&recognitionSite=&matchType=1.*
Chiang et al. (2009) "High-resolution mapping of copy-number alterations with massively parallel sequencing" Nature Methods 6(1): 99-103.*
Wang et al. (2012) "2b-RAD: a simple and flexible method for genome-wide genotyping" Nature Methods 9(8):808-810.*
Hsieh et al. (2015) "Mapping Nucleosome Resolution Chromosome Folding in Yeast by Micro-C." Cell 162(1):108-119, including Supplemental Procedures and Table S1.*
Sudmant et al. (2015) "An integrated map of structural variation in 2,504 human genomes" Nature 526(7571):75-81.*
Bosch et al., Keeping Up With the Next Generation, J Mol Diagn. Nov. 2008; 10(6): 484-492.
Campbell et al. Identification of somatically acquired rearrangements in cancer using genome-wide massively parallel paired-end sequencing, Nat Genet. Jun. 2008; 40(6): 722-729.
Talkowski et al. Next-Generation Sequencing Strategies Enable Routine Detection of Balanced Chromosome Rearrangements for Clinical Diagnostics and Genetic Research, The American Journal of Human Genetics. Apr. 2011; 88, 469-481.
Schmitt et al. Detection of ultra-rare mutations by next-generation sequencing. Proc Natl Acad Sci U S A. Sep. 4, 2012; 109(36): 14508-14513.
Ge et al. Copy Number variation in the cattle genome. Funct Integr Genomics. Nov. 2012;12(4):609-24.
Kidd et al. Mapping and sequencing of structural variation from eight human genomes. Nature. May 1, 2008; 453(7191): 56-64.
Druley et al. Quantification of rare allelic variants from pooled genomic DNA. Nature Methods. 2009; 6, 263-265.
Velculescu et al. Serial Analysis of Gene Expression. Science. 1995. 270, 484.
Coco et al. DNA shuffling method for generating highly recombined genes and evolved enzymes. Nat Biotechnol. Apr. 2001;19(4):354-9.
Craig et al. Identification of genetic variants using bar-coded multiplexed sequencing. Nat Methods. Oct. 2008 ; 5(10): 887-893.
Stemmer et al. DNA shuffling by random fragmentation and reassembly: in vitro recombination for molecular evolution. Proc Natl Acad Sci U S A. Oct. 25, 1994;91(22):10747-51.
Sen et al. Developments in directed evolution for improving enzyme functions. Appl Biochem Biotechnol. Dec. 2007;143(3):212-23.
Communication forwarding Extended European Search Report, issued by the European Patent Office dated Feb. 18, 2019, concerning counterpart European Patent Application No. 16845040.1.
Ansorge, William J. (2009) "Next-generation DNA sequencing techniques", New Biotechnology 25(4):195-203.
Malhotra and Sebat (2012) "CNVs: Harbingers of a Rare Variant Revolution in Psychiatric Genetics", Cell 148(6):1223-1241.
Wang et al. (2016) "SMASH, a fragmentation and sequencing method for genomic copy number analysis", Genome Res. 26:844-851.
Warburton et al. (2013) "The contribution of de novo and rare inherited copy number changes to congenital heart disease in an unselected sample of children with conotruncal defects or hypoplastic left heart disease", Hum Genet 133:11-27.
Weischenfeldt et al. (2013) "Phenotypic impact of genomic structural variation: insights from and for human disease", Genetics 14:125-138.

* cited by examiner

A  MAM mapping and read decomposition
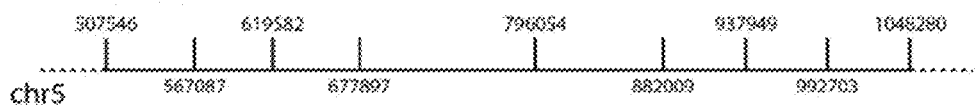
B  determine bin boundaries
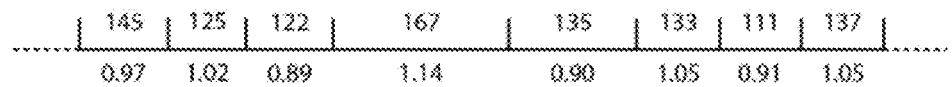
C  count maps per bin and normalize
| 145 | 125 | 122 | 167 | 135 | 133 | 111 | 137 |
| --- | --- | --- | --- | --- | --- | --- | --- |
| 0.97 | 1.02 | 0.89 | 1.14 | 0.90 | 1.05 | 0.91 | 1.05 |
D  LOESS normalization for GC
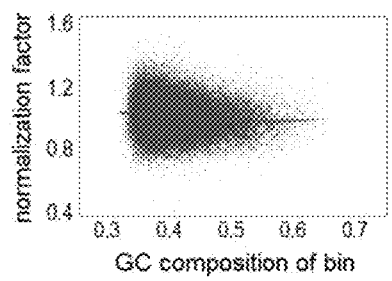
E  circular binary segmentation (CBS)
Figs. 2A-2E

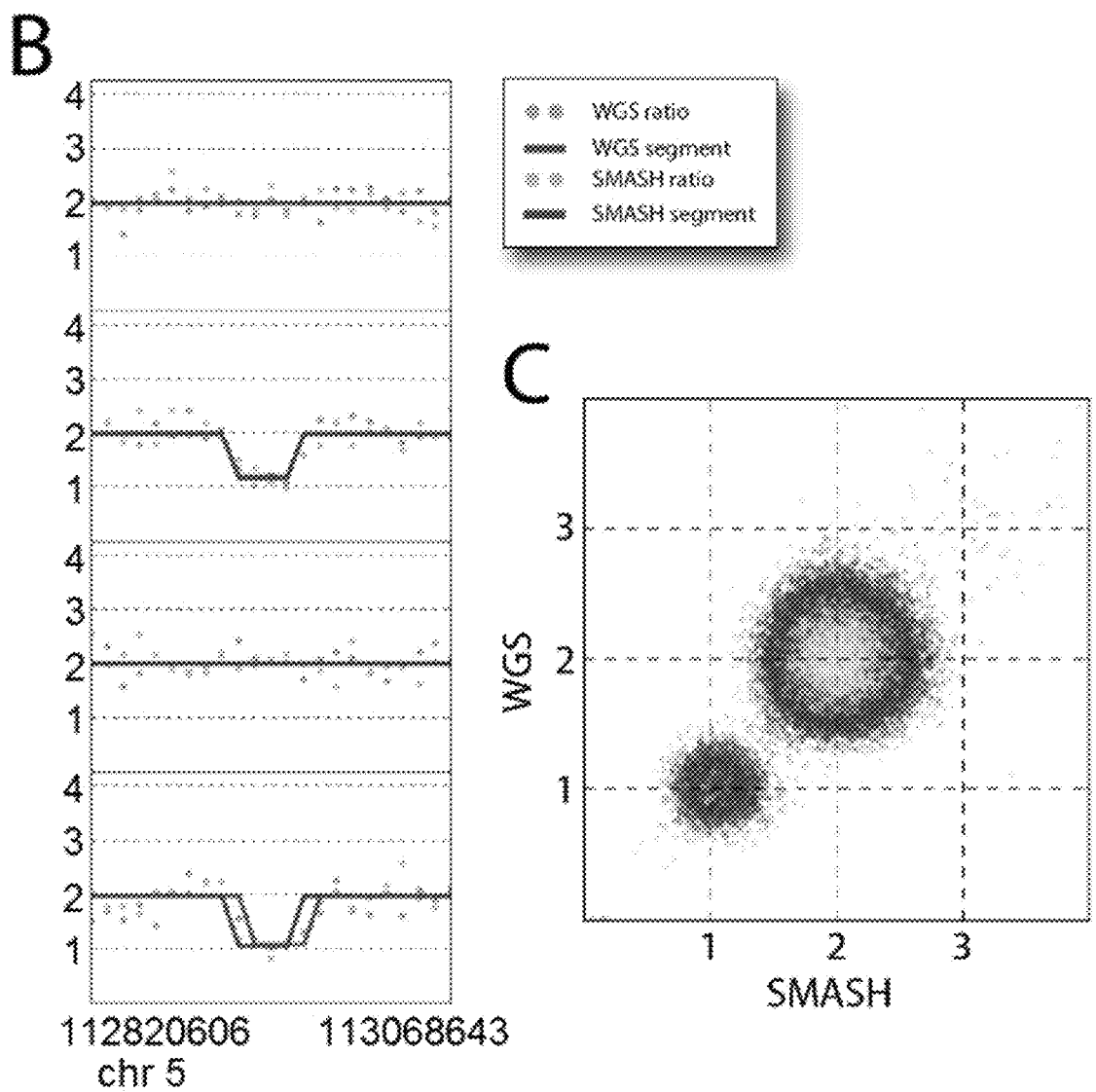
Figs. 3B-C

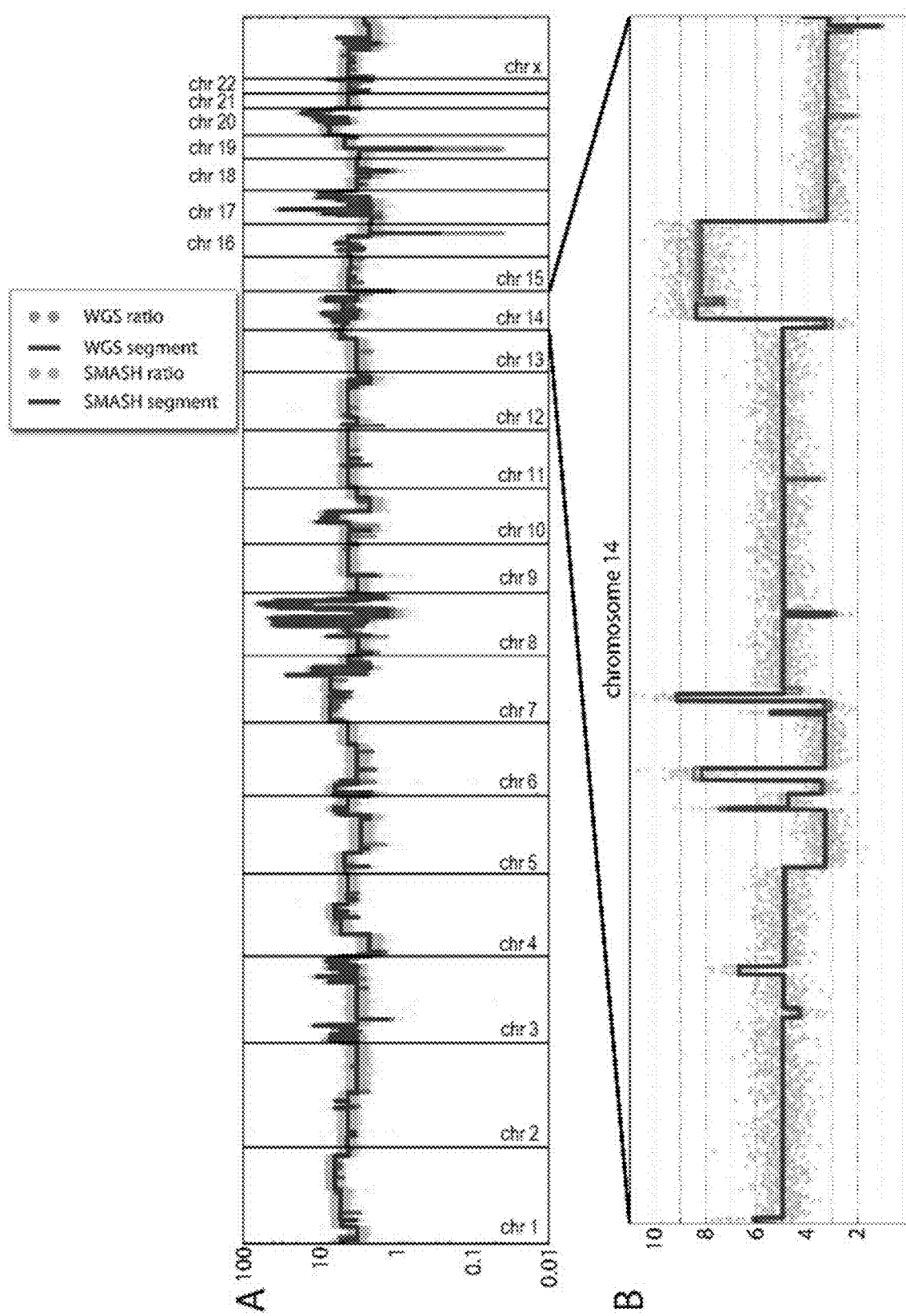
Figs. 4A-B

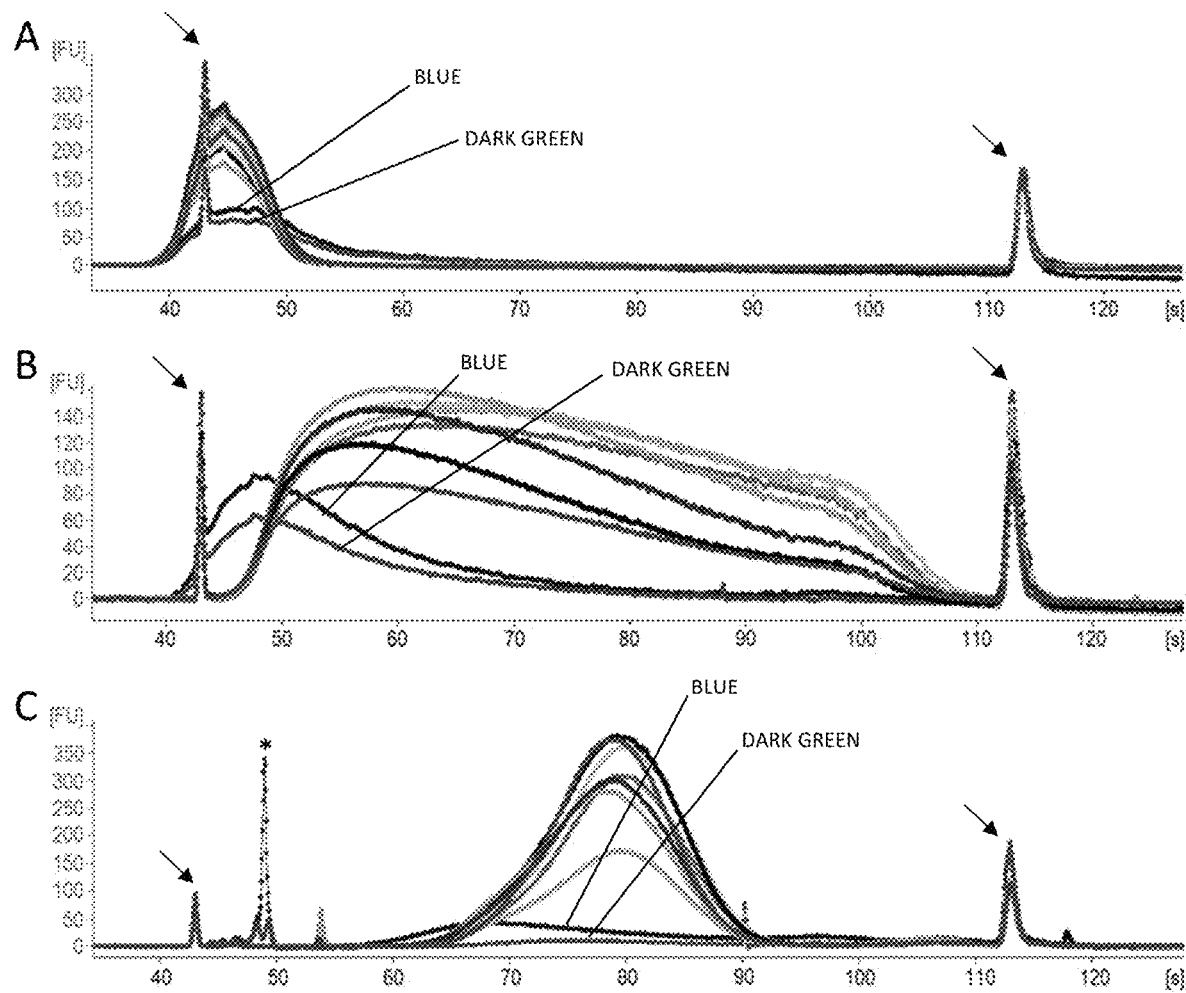
Figs. 5A-C

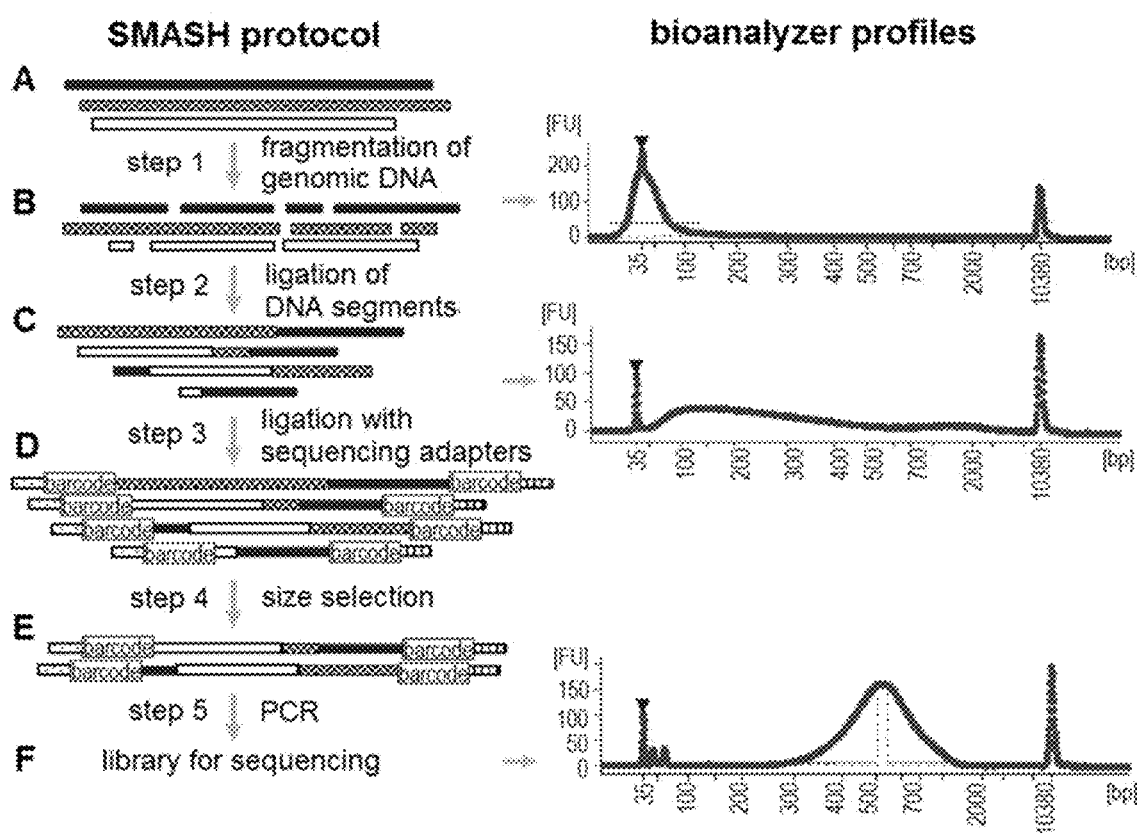
Figs. 6A-F

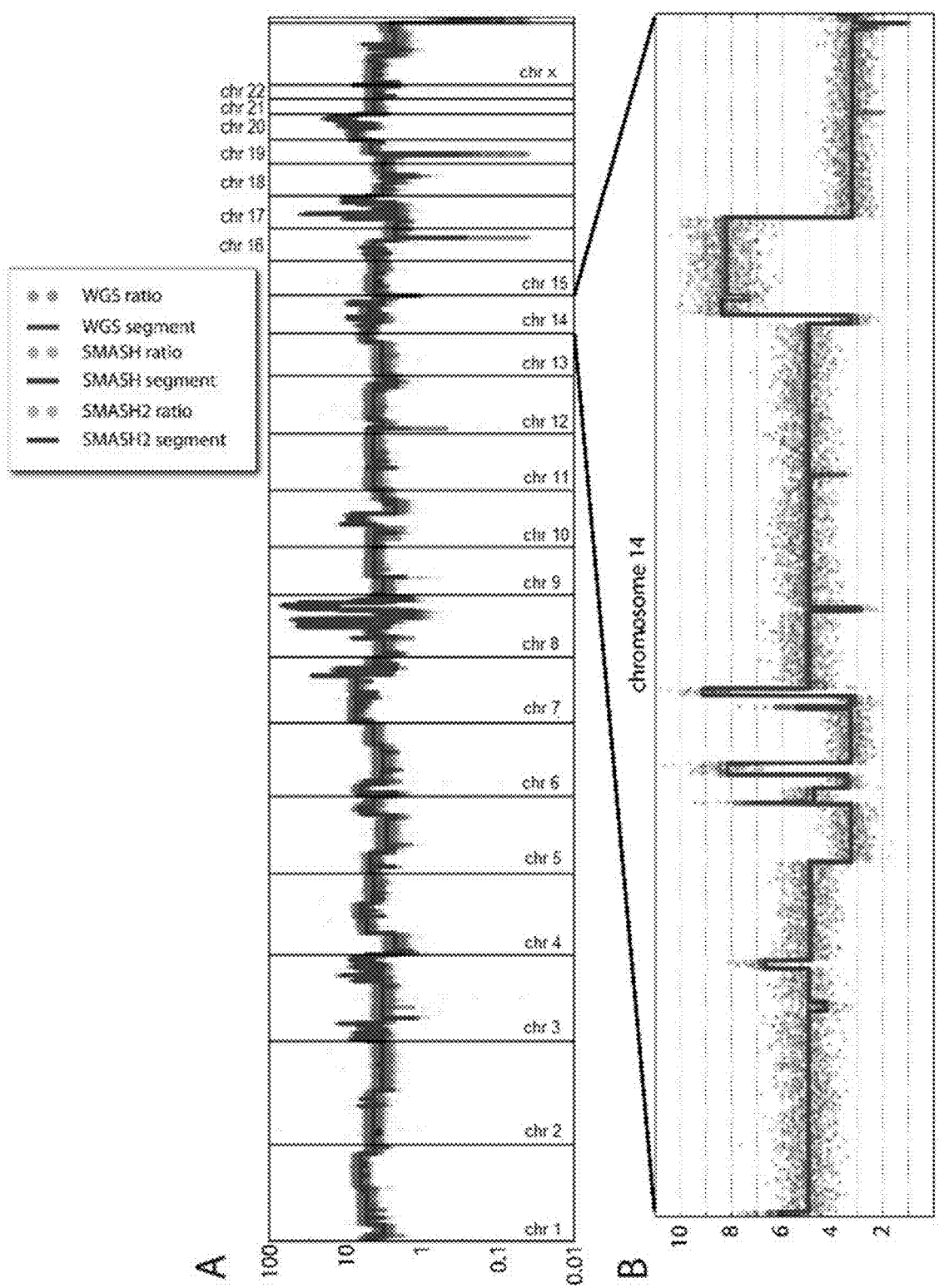
Figs. 7A-B

SEQUENCE LISTING

```
<160> NUMBER OF SEQ ID NOS: 10

<210> SEQ ID NO 1
<211> LENGTH: 143
<212> TYPE: DNA
<213> ORGANISM: Homo sapiens

<400> SEQUENCE: 1
gcccccttac cacactacac tctcagaatg ttctaagcag gatatgagag gagtgtattc      60
tcggggactc atagggttgt tttgaagatt aaataagttc gcccactcag ggcagtaaca     120
ccagaccagt gagaaagatc agt                                             143

<210> SEQ ID NO 2
<211> LENGTH: 143
<212> TYPE: DNA
<213> ORGANISM: Homo sapiens

<400> SEQUENCE: 2
ctggggttat aggaggactg gatgatgatg actaaggaag gaatgagact tttgacatag      60
aagatagctg attaatttt gttcttcttt gtatgaatga acttttttgat aatcaccaag     120 aagctttcag gaaatcaagg atg                                             143

<210> SEQ ID NO 3
<211> LENGTH: 66
<212> TYPE: DNA
<213> ORGANISM: Homo sapiens

<400> SEQUENCE: 3
gcccccttac cacactacac tctcagaatg ttctaagcag gatatgagag gagtgtattc      60
tcgggg                                                                66

<210> SEQ ID NO 4
<211> LENGTH: 36
<212> TYPE: DNA
<213> ORGANISM: Homo sapiens
```

```
<400> SEQUENCE: 4
gactcatagg gttgttttga agattaaata agttcg                              36

<210> SEQ ID NO 5
<211> LENGTH: 43
<212> TYPE: DNA
<213> ORGANISM: Homo sapiens

<400> SEQUENCE: 5
gcccactcag ggcagtaaca ccagaccagt gagaaagatc agt                      43

<210> SEQ ID NO 6
<211> LENGTH: 39
<212> TYPE: DNA
<213> ORGANISM: Homo sapiens

<400> SEQUENCE: 6
ctggggttat aggaggactg gatgatgatg actaaggaa                           39

<210> SEQ ID NO 7
<211> LENGTH: 29
<212> TYPE: DNA
<213> ORGANISM: Homo sapiens

<400> SEQUENCE: 7
ggaatgagac ttttgacata gaagatagc                                      29

<210> SEQ ID NO 8
<211> LENGTH: 59
<212> TYPE: DNA
<213> ORGANISM: Homo sapiens

<400> SEQUENCE: 8
gctgattaat ttttgttctt ctttgtatga atgaactttt tgataatcac caagaagct     59

<210> SEQ ID NO 9
<211> LENGTH: 23
<212> TYPE: DNA
<213> ORGANISM: Homo sapiens

<400> SEQUENCE: 9
aagctttcag gaaatcaagg atg                                            23

<210> SEQ ID NO 10
<211> LENGTH: 20
<212> TYPE: DNA
<213> ORGANISM: Homo sapiens

<400> SEQUENCE: 10
ccaagaagct ttcaggaaat                                                20
```

GENETIC COPY NUMBER DETERMINATION USING HIGH THROUGHPUT MULTIPLEX SEQUENCING OF SMASHED NUCLEOTIDES

This application claims priority of U.S. Provisional Application Nos. 62/292,151, filed Feb. 5, 2016, 62/250,405, filed Nov. 3, 2015 and 62/215,540, filed Sep. 8, 2015, the contents of which are hereby incorporated by reference.

This application incorporates-by-reference nucleotide and/or amino acid sequences which are present in the file named "170906_5981_87857_PCT_US_Sequence_Listing_ AWG.txt", which is 104.0 kilobytes in size, and which was created Sep. 6, 2017 in the IBM-PC machine format, having an operating system compatibility with MS-Windows, which is contained in the text file filed Sep. 6, 2017 as part of this application.

Throughout this application, various publications are referenced, including referenced in parenthesis. Full citations for publications referenced in parenthesis may be found listed at the end of the specification immediately preceding the claims. The disclosures of all referenced publications in their entireties are hereby incorporated by reference into this application in order to more fully describe the state of the art to which this invention pertains.

BACKGROUND OF INVENTION

Analysis of copy number variants (CNVs) on a genomic scale is useful for assessing cancer progression and identifying congenital genetic abnormalities. CNVs are typically identified by microarray hybridization, but can also be detected by next-generation sequencing (NGS) (Alkan et al., 2009; Sudmant et al., 2010). This is generally done using algorithms that measure the number of sequence reads mapping to specific regions. Consequently, the resolution of sequence-based copy number methods depends largely on the number of independent mappings.

The current trend in next generation sequencing technologies is to increase the number of bases read per unit cost. This is accomplished by increasing the total number of sequence reads per lane of a flow cell, as well as increasing the number of bases within each read. Because the accuracy of copy number determination methods is driven by the quantity of independent reads, increased length of sequence reads does not improve the resolution of copy number analysis. Most of the genome is mapped well by short reads, on the order of 25-30 base pairs (bp). At the moment, high throughput sequencers are generating read lengths of ~150 bp, well in excess of what would suffice for unique mapping.

SUMMARY OF THE INVENTION

To take advantage of increasing read lengths, SMASH (Short Multiply Aggregated Sequence Homologies) was developed as a technique optimized for packing multiple independent mappings into every read. This is accomplished by breaking genomic DNA into small but still mappable segments, with a mean length of ~40 bp. These small segments are combined into chimeric fragments of DNA of lengths suitable for creating NGS libraries (300-700 bp).

The chimeric sequence reads generated by SMASH are processed using a time-efficient, memory-intensive mapping algorithm that performs a conservative partition of the long fragment read into constituent segment maps. The segment maps are utilized in the same manner as read maps in downstream copy number analysis. For 150-bp paired-end reads, the most cost-efficient sequencing platform so far, whole genome sequencing (WGS) averages less than one map per read pair, whereas SMASH averages >4. The quality of SMASH maps, i.e. the non-uniformities introduced by the sample preparation, sequencer and mapping bias, are of the same order as those seen with WGS mapping. Using correction and testing protocols most favorable to WGS data, map-for-map SMASH was shown to generate nearly equivalent quality copy number data as WGS at a fraction of the cost.

Figures 1A, 1B, 1C, 1D, 1E, 1F:
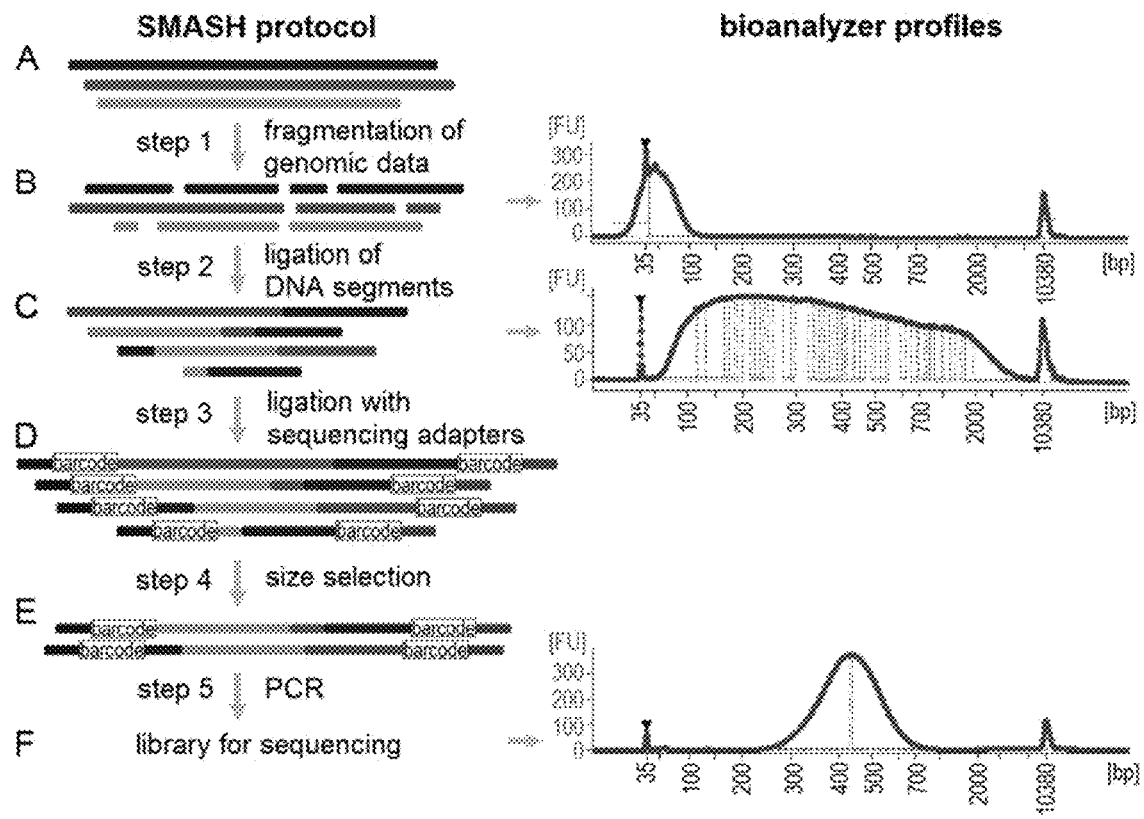
FIG. 1. Schematic of the SMASH method and size analysis.

A) Three representative genomic DNA molecules, shown in black, white and checkered boxes, originate from different chromosomes or distant regions of the same chromosome. B) By sonication and restriction enzyme cleavage, these molecules are fragmented into short double-stranded DNA segments with average length of 40-50 bp, as shown in the bioanalyzer result at right. C) These short DNA segments are then partially end-repaired and combined into longer fragments of DNA with lengths ranging from 50 bp to 7 kb. Hence, each resulting chimeric DNA fragment contains short DNA segments from different locations (shown by the varying box styles described above). D) These DNA fragments are ligated to sequencing adaptors containing sample barcodes, shown in dotted and vertically striped boxes, with the "barcode" box designating the sample barcodes. E) Size selection is carried out to enrich for DNA fragments in the size range of 250-700 bp, which is confirmed in the bioanalyzer. F) After final PCR, libraries are ready for sequencing.

FIG. 2. SMASH informatics pipeline.

Panel A shows the decomposition of a read pair GCCCCCTTACCACACTACACTCTCAGAATGT-TCTAAGCAGGATATGAGAGGAGTGTATTCTC GGGGACTCATAGGGTTGTTTTGAAGAT-TAAATAAGTTCGCCCACTCAGGGCAGTAACACCAG ACCAGTGAGAAAGATCAGT (SEQ ID NO: 1) and CTGGGGTTATAGGAGGACTGGATGATGAT-GACTAAGGAAGGAATGAGACTTTTGACATAGAA GATAGCTGATTAATTTTTGTTCTTCTTTGTATGAAT-GAACTTTTTGATAATCACCAAGAAGC TTTCAG-GAAATCAAGGATG (SEQ ID NO: 2) into a set of maximal uniquely mappable segments GCCCCCTTACCACACTA-CACTCTCAGAATGTTCTAAGCAGGATATGAGAG-GAGTGTATTCTC GGGG (SEQ ID NO: 3), GACT-CATAGGGTTGTTTTGAAGATTAAATAAGTTCG (SEQ ID NO: 4), GCCCACTCAGGGCAGTAACACCAGAC-CAGTGAGAAAGATCAGT (SEQ ID NO: 5), CTGGGGT-TATAGGAGGACTGGATGATGATGACTAAGGAA (SEQ ID NO: 6), GGAATGAGACTTTTGACATAGAAGATAGC (SEQ ID NO: 7), GCTGATTAATTTTTGTTCTTCTTTG-TATGAATGAACTTTTTGATAATCACCAAGAAGCT (SEQ ID NO: 8), and AAGCTTTCAGGAAAT-CAAGGATG (SEQ ID NO: 9). In contrast to the map indicated by the arrow i.e., CCAAGAAGCTTTCAG-GAAAT (SEQ ID NO: 10), the other maps satisfy the "20,4" rule (see text) and are considered countable maps. Panel B shows a stretch of chromosome 5 with bin boundaries selected so that each bin has the same number of exact matches from all 50-mers from the reference genome. Excluding duplicate reads, the number of "20,4" mappable segments present in each bin is counted in panel C. LOESS normalization is used to adjust bin counts for sample-specific GC bias (panel D). Lastly, in panel E, the data is segmented using circular binary segmentation (CBS) of the GC normalized data.

FIG. 3. SMASH and WGS copy number profiles for an SSC quad.

Panel A shows the whole genome view (autosome and X chromosomes) for the four members of a family. The dots show the reference and GC normalized ratio values for WGS and SMASH. Similarly, the overlapping lines show the copy number segmentation by CBS (circular binary segmentation) for both WGS and SMASH. The black box highlights a deletion on chromosome 5 that is expanded in panel B. The deletion, identified by both methods, occurs in the father and is transmitted to the sibling in the family. Panel C illustrates the bin for bin comparison of the normalized ratio values of the father from WGS and SMASH. The dark and light points show increasingly sparse subsamples of the data points.

FIG. 4. SMASH and WGS copy number profiles for SKHR3.

The SKBR3 breast cancer cell line has a complex copy number pattern. Panel A shows the whole genome view with copy number on a log scale. The dots show the GC-normalized ratio values for WGS and SMASH, while the overlapping lines show the copy number segmentation for both WGS and SMASH. Panel B expands on chromosome 14 on a linear scale. There is strong agreement between WGS and SMASH in the integer copy number state segmentations and dispersion about the segment mean. Panel C illustrates the bin for bin comparison of the normalized ratio values from WGS and SMASH. The dark and light points show increasingly sparse subsamples of the data points to illustrate density.

FIG. 5. Bioanalyzer results of SMASH protocols on independent samples.

Following FIG. 1, right panel, we show bioanalyzer results of SMASH protocols on independent samples. Lower (35 bp) and upper markers (10.38 kb) are indicated by arrows. In each panel, two of the ten profiles (in blue and dark green) show results for bad quality DNA samples. The remaining curves are of good quality. (A) Size distribution of DNA molecules after DNA fragmentation. Blue and dark green curves show a wider length range and longer average length of DNA segments than the remaining samples. (B) After random ligation of DNA segments, curves from good samples show a wide length range of DNA concatemers. (C) For the final DNA library, curves from good samples show the length range from 250 bp-700 bp, ideal for sequencing. The failed libraries show mainly sequencing adaptor dimers, highlighted with a star.

FIG. 6. Schematic of alternative SMASH method (left panel) and bioanalyzer results (right panel).

In bioanalyzer results, x-axis represents the length of DNA segments. (A) Three genomic DNA molecules, shown in black, white and checkered boxes, are from different chromosomes or different locations of the same chromosome. (B) By dsDNA fragmentase cutting, these DNA molecules are fragmented into short double-stranded segments with average length around 35 bp, as shown in bioanalyzer result on right panel. (C) Then these short DNA segments are partially end-repaired and randomly concatenated into longer fragments of DNA with length range from 50 bp to 7 kb. Hence, each DNA fragment contains several short DNA segments that are from different locations/chromosomes shown in different box styles as described above. (D) These DNA fragments are ligated with sequencing adaptors containing sample barcodes, shown in dotted and vertically striped boxes linked with an open box labeled "barcode". (E) Size selection is carried out to make DNA fragments in the proper size range from 250 bp to 700 bp, which is confirmed in the bioanalyzer result of the final DNA library. (F) After final PCR by sequencing adaptors, libraries are ready for sequencing.

FIG. 7. SMASH2 compared to WGS and SMASH on SKBR3.

Similar to FIG. 4, panels A and B, the agreement of the newer SMASH protocol (SMASH2) with both WGS and the previous SMASH protocol is shown. There is excellent agreement between the three methods.

DETAILED DESCRIPTION OF THE INVENTION

SMASH reduces genomic DNA to small but still uniquely mappable segments, and randomly ligates them into chimeric stretches of DNA of lengths suitable for creating next-generation sequencing (NGS) libraries (400-500 bp). Sequencing of these libraries results in a paradigm in which CNVs can be detected through template analysis (Levy and Wigler, 2014). The crux of its significance lies in its efficiency: SMASH can be run on average NGS instruments and yield ~6 times or more as many maps as 'standard' whole genome sequencing (WGS). On a machine that generates 300 million 150-bp paired-end reads, SMASH can obtain 60 million maps per sample at a resolution of ~10 kb.

Specifically, genomic DNA is cleaved ('smashed') into small but mappable segments by sonication and/or enzymatic activity, with a mean length of ~40 bp, then ligated into longer chimeric fragments of DNA.

A second fragmentation step eliminates long (>1 kb) chimeric molecules, and fragments suitable for creating NGS libraries are purified (e.g. 400-500 bp). Barcoded sequencing adaptors are added to create libraries that can be multiplexed on a single sequencing lane, significantly reducing cost/patient. To obtain mapping information from the chimeric reads, we apply an algorithm and a set of heuristics. Suffix arrays adapted from sparseMEM (Khan et al., 2009) are used to determine 'maximal almost-unique matches' (MAMs) between a NGS read and the reference genome. The mappings within a read pair provide a unique signature for each read, allowing identification and removal of PCR duplicates. CNV detection is based on map-counting methods, employing bins of expected uniform density (Navin et al., 2011). For each sample, we count the number of maps within each bin, then adjust bin counts for GC bias by LOESS normalization. Template analysis (Levy and Wigler, 2014) is utilized to overcome distinct patterns of systematic noise that extend beyond the gross-scale corrections of GC adjustment, which is inherent in both WGS and SMASH reads. The result of these measurements is an ability to detect CNV on par with WGS.

The present invention provides a composition comprising a first mixture of different chimeric genomic nucleic acid fragments, wherein each different fragment in the mixture comprises randomly ligated DNA segments, wherein each DNA segment in the fragment is a nucleic acid molecule at least 27 base pairs in length resulting from random fragmentation of a single genome.

In some embodiments, wherein the segments are ligated directly to each other to form a fragment.

In some embodiments, wherein the DNA segments are about 30 to 50 base pairs in length.

In some embodiments, wherein at least 50% of the segments in the fragment are about 30 to 50 base pairs in length.

In some embodiments, enriched for chimeric genomic nucleic acid fragments less than about 1000 base pairs in length.

In some embodiments, enriched for chimeric genomic nucleic acid fragments about 250 to about 700 base pairs in length, preferably 400-500 base pairs.

In some embodiments, wherein at least 50% of the chimeric genomic nucleic acid fragments in the mixture are about 250 to about 700 base pairs in length, preferably 400-500 base pairs.

In some embodiments, wherein the mixture of different chimeric genomic nucleic acid fragments contains at least 1,000 different fragments.

In some embodiments, wherein the mixture of different chimeric genomic nucleic acid fragments contains at least 10,000 different fragments.

In some embodiments, wherein the mixture of different chimeric genomic nucleic acid fragments contains at least 100,000 different fragments.

In some embodiments, wherein the mixture of different chimeric genomic nucleic acid fragments contains fragments composed of an odd number of segments.

In some embodiments, wherein the mixture of chimeric genomic nucleic acid fragments contain ligated segments whose two ligation points form a sequence other than a restriction enzyme recognition site.

In some embodiments, further comprising sequence adaptors ligated to the termini of the chimeric genomic nucleic acid fragments.

In some embodiments, a sequence adaptor ligated to the termini of the chimeric genomic nucleic acid fragments comprises a barcode identifying the genomic source of the fragment.

In some embodiments, a sequence adaptor ligated to the termini of the chimeric genomic nucleic acid fragments comprises primer binding site for amplification.

In some embodiments, enriched for sequence adaptor-ligated chimeric genomic nucleic acid fragments about 250 to about 700 base pairs in length, preferably 400-500 base pairs.

In some embodiments, comprising amplified sequence adaptor-ligated chimeric genomic nucleic acid fragments. Such amplification may be accomplished by methods such as PCR. Primer binding for accomplishing this amplification step may be located on the ligated sequencing adaptor.

In some embodiments, further comprising a second mixture of different chimeric genomic nucleic acid fragments, wherein the second mixture of fragments is obtained from a different genome than the first mixture.

In some embodiments, comprising a collection of multiple mixtures of different chimeric genomic nucleic acid fragments, wherein each mixture of fragments in the collection is obtained from a different genome than any other mixture in the collection.

In some embodiments, wherein each mixture of chimeric genomic nucleic acid fragments contains fragments having a sequencing adaptor containing a unique barcode ligated onto only fragments within the mixture, such that the collection of mixtures can be multiplexed.

In some embodiments, wherein the genomic nucleic acids are extracted from a cell, a tissue, a tumor, a cell line or from blood.

In some embodiments, a method for obtaining a mixture of different chimeric genomic nucleic acid fragments from a single genome, comprising
i) randomly fractionating the single genome to obtain random segments from the genome; and ii) subjecting the segments from step (i) to ligation to generate different chimeric genomic nucleic acid fragments, thereby obtaining the mixture of different genomic nucleic acid fragments from the single genome.

In some embodiments, further comprising size selecting a subpopulation of segments about 30 to 50 base pairs in length prior to ligation.

In some embodiments, wherein the subpopulation of segments is selected using bead purification.

In some embodiments, wherein in step (i) the genomic nucleic acids are mechanically sheared to obtain the randomly fragmented DNA segments.

In some embodiments, wherein the mechanical shearing is by sonication.

In some embodiments, further comprising subjecting the segments of genomic nucleic acids to enzymatic digestion.

In some embodiments, wherein the enzymatic digestion of the segments of genomic nucleic acids is by the restriction enzymes CvikI-1 and NlaIII.

In some embodiments, wherein in step (i) genomic nucleic acids are enzymatically fragmented, by
a) generating random DNA nicks in the genome; and
b) cutting the DNA strand opposite the nick,
thereby producing dsDNA breaks in the genomic nucleic acids resulting in DNA segments.

In some embodiments, wherein the resulting DNA segments are end-repaired directly after genomic fragmentation.

In some embodiments, wherein chimeric genomic nucleic acid fragments are end-repaired after their formation by random segment ligation In some embodiments, further comprising reducing the size of the chimeric genomic nucleic acid fragments.

In some embodiments, further comprising selecting for fragments about 250 to about 700 base pairs in length.

In some embodiments, further comprising purifying the chimeric genomic nucleic acid fragments, optionally by bead purification.

The method of any one of claims 20-32, further comprising adenylating the 3' termini of the chimeric genomic nucleic acid fragments.

In some embodiments, further comprising ligating sequencing adaptors to the chimeric genomic nucleic acid fragments.

In some embodiments, further comprising purifying the sequence adaptor-ligated genomic nucleic acid fragments, optionally by purification.

In some embodiments, further comprising selecting for sequence adaptor-ligated genomic nucleic acid fragments about 250 to about 700 base pairs in length.

In some embodiments, further comprising amplifying the size-selected sequence adaptor-ligated genomic nucleic acid fragments.

In some embodiments, further comprising ligating a unique adaptor barcode to a mixture of chimeric genomic nucleic acid fragments from the same genome, such that multiplex sequencing can be performed upon pooling of multiple mixtures from different genomes.

In some embodiments, wherein the initial amount of genomic nucleic acids is about 200 ng, 500 ng, or 1 µg.

In some embodiments, wherein the genomic nucleic acids are extracted from a cell, a tissue, a tumor, a cell line or from blood.

In some embodiments, wherein sequences are obtained from a mixture of chimeric genomic nucleic acid fragments using a next-generation sequencing platform.

In some embodiments, a process of obtaining the nucleic acid sequence of the different chimeric genomic nucleic acid fragments of the composition described above, or produced by the process described above, comprising (i) obtaining the fragments, and (ii) sequencing the fragments, so as to obtain the nucleic acid sequence of the different chimeric genomic nucleic acid fragments.

In some embodiments, nucleic acid sequence information obtained by the process described above.

In some embodiments, a process for obtaining genomic copy number information from a genome, comprising
  i) obtaining the nucleic acid sequence of the different chimeric genomic nucleic acid fragments of the composition described above, or produced by the process described above;
  ii) identifying and mapping to a genome each Maximal Almost-unique Match (MAM) within a sequenced chimeric genomic nucleic acid fragment; and
  iii) counting the number of mapped MAMs within a binned genome, thereby obtaining genomic copy number information.

In some embodiments, wherein in step (ii) MAMs are identified using a longMEM software package.

In some embodiments, wherein step (ii) further comprises filtering MAMs by discarding MAMs less than twenty basepairs and not at least four basepairs longer than required for uniqueness.

In some embodiments, wherein step (ii) further comprises filtering MAMs by discarding MAMs in a read-pair map that are within 10,000 basepairs of one another.

In some embodiments, wherein in step (iii) the number of mapped reads are counted in genome bin sizes that yield uniform map counts for the reference sample.

In some embodiments, wherein in step (iii) the number of mapped reads are counted in empirically determined genome bins of uniform observation of a reference.

In some embodiments, wherein in step (iii) the number of mapped reads are counted in genome bins of expected uniform density.

In some embodiments, wherein in step (iii) the number of mapped reads in each bin is adjusted for GC bias by LOESS normalization.

In some embodiments, wherein in step (iii) template analysis is utilized to reduce systematic noise in GC adjusted bin count data.

In some embodiments, wherein in step (iii) a reference normalization is applied to bin count data by dividing GC-adjusted bin ratios by a standard sample bin ratio.

In some embodiments, wherein in step (iii), reference normalized GC-adjusted bin count data is analyzed by circular binary segmentation.

In some embodiments, wherein in step (iii) the total number of reference maps is matched to the total number of sample maps.

In some embodiments, genomic copy number information obtained by any of the processes described above.

In some embodiments, A method of diagnosing, predicting likelihood of displaying or determining the probability of inheriting a prenatal disorder, a pediatric disorder, a developmental disorder, a psychological disorder, an autoimmune disorder, cancer, congenital heart disease, schizophrenia, Autism Spectrum Disorders or a patient's response to a therapy, comprising obtaining the patient's genomic copy number information.

In some embodiments, a method of treating a patient comprising obtaining the patient's genomic copy number information, and treating the patient consistent with the patient's genomic copy number information.

The present invention also provides for the use of a patient's genomic copy number information obtained according to the present invention in treating the patient consistent with, or developing a treatment for the patient consistent with, the patient's genomic copy number information.

The present invention also provides a patient's genomic copy number information obtained according to the present invention for use in treating the patient consistent with, or developing a treatment for the patient consistent with, the patient's genomic copy number information.

Each embodiment disclosed herein is contemplated as being applicable to each of the other disclosed embodiments. Thus, all combinations of the various elements described herein are within the scope of the invention.

Terms

Unless otherwise defined, all technical and scientific terms used herein have the same meaning as commonly understood by a person of ordinary skill in the art to which this invention belongs.

As used herein, and unless stated otherwise or required otherwise by context, each of the following terms shall have the definition set forth below.

As used herein, "about" in the context of a numerical value or range means±10% of the numerical value or range recited or claimed, unless the context requires a more limited range.

The terms "nucleic acid molecule" and "sequence" are not used interchangeably herein. A "sequence" refers to the sequence information of a "nucleic acid molecule".

The terms "template", "nucleic acid", and "nucleic acid molecule", are used interchangeably herein, and each refers to a polymer of deoxyribonucleotides and/or ribonucleotides. "Nucleic acid" shall mean any nucleic acid, including, without limitation, DNA, RNA and hybrids thereof. The nucleic acid bases that form nucleic acid molecules can be the bases A, C, G, T and U, as well as derivatives thereof. "Genomic nucleic acid" refers to DNA derived from a genome, which can be extracted from, for example, a cell, a tissue, a tumor or blood.

As used herein, the term "chimeric" refers to being comprised of nucleic acid molecules taken from random loci within a genome that are reconnected in a random order. In SMASH, a fragment is considered to be chimeric because it is a composed of randomly ligated segments of a genome.

As used herein, the term "fragmentation" refers to the breaking up of large nucleic acids e.g. genomic DNA into smaller stretches of nucleotides. Fragmentation can be accomplished by multiple methods including but not limited to, sonication and enzymatic activity.

As used herein "contig" and "contiguous" refers to a set of overlapping sequence or sequence reads.

As used herein, the term "amplifying" refers to the process of synthesizing nucleic acid molecules that are complementary to one or both strands of a template nucleic acid. Amplifying a nucleic acid molecule typically includes denaturing the template nucleic acid, annealing primers to the template nucleic acid at a temperature that is below the melting temperatures of the primers, and enzymatically elongating from the primers to generate an amplification product. The denaturing, annealing and elongating steps each can be performed once. Generally, however, the denaturing, annealing and elongating steps are performed multiple times (e.g., polymerase chain reaction (PCR)) such that the amount of amplification product is increasing, often times exponentially, although exponential amplification is not required by the present methods. Amplification typically requires the presence of deoxyribonucleoside triphosphates, a DNA polymerase enzyme and an appropriate buffer and/or co-factors for optimal activity of the polymerase enzyme. The term "amplified nucleic acid molecule" refers to the nucleic acid molecules, which are produced from the amplifying process.

As used herein, the term "mapping" refers to identifying a unique location on a genome or cDNA library that has a sequence which is substantially identical to or substantially fully complementary to the query sequence. A nucleic acid molecule containing a sequence that is capable of being mapped is considered "mappable." The nucleic acid molecule may be, but is not limited to the following: a segment of genomic material, a cDNA, a mRNA, or a segment of a cDNA.

As used herein, the term "read" or "sequence read" refers to the nucleotide or base sequence information of a nucleic acid that has been generated by any sequencing method. A read therefore corresponds to the sequence information obtained from one strand of a nucleic acid fragment. For example, a DNA fragment where sequence has been generated from one strand in a single reaction will result in a single read. However, multiple reads for the same DNA strand can be generated where multiple copies of that DNA fragment exist in a sequencing project or where the strand has been sequenced multiple times. A read therefore corresponds to the purine or pyrimidine base calls or sequence determinations of a particular sequencing reaction.

As used herein, the terms "sequencing", "obtaining a sequence" or "obtaining sequences" refer to nucleotide sequence information that is sufficient to identify or characterize the nucleic acid molecule, and could be the full length or only partial sequence information for the nucleic acid molecule.

As used herein, the term "reference genome" refers to a genome of the same species as that being analyzed for which genome the sequence information is known.

As used herein, the term "region of the genome" refers to a continuous genomic sequence comprising multiple discrete locations.

As used herein, the term "sample tag" refers to a nucleic acid having a sequence no greater than 1000 nucleotides and no less than two that may be covalently attached to each member of a plurality of tagged nucleic acid molecules or tagged reagent molecules. A "sample tag" may comprise part of a "tag."

As used herein, the term "segment" of genomic material refers to the mappable nucleic acid molecules resulting from random fragmentation of genomic DNA. A segment in a SMASH fragment are about 30 to 50 base pairs in length, and may for example have a length of 27, 28, 29, 30, 31, 32, 33, 34, 35, 36, 37, 38, 39, 40, 41, 42, 43, 44, 45, 46, 47, 48, 49 or 50 base pairs.

As used herein, the term "fragment" refers to a chimeric DNA molecule resulting from the ligation of multiple DNA segments. Thus, as used herein, a "fragment" contains at least one and usually more than one "segment," preferably 2, 3, 4, 5, 6, 7, 8, 9 or 10 segments. Although methods described herein provide segments of highly uniform length, a fragment may contain segments having lengths outside of the preferred size range of 30 to 50 base pairs.

As used herein the term "sequencing library" refers to a mixture of DNA fragments comprising the total genomic DNA from a single organism for use in sequencing. Next-generation sequencing libraries are generally size-selected and ligated to sequencing adaptors prior to sequencing. Steps in next-generation sequencing library preparation may include fragmentation, end-repairing, adenylation, sequencing adaptor ligation and PCR enrichment. A number of purification and size-selection steps may also be performed throughout the next-generation sequencing library preparation. Specifically, a "SMASH library" refers to a type of sequencing library which is composed of a mixture of fragments of genomic DNA from a single organism, wherein the fragments are chimeric nucleic acid molecules made up of smaller, yet mappable, randomly ligated segments of the genomic DNA.

As used herein the term "ligation" refers to the enzymatic joining of two nucleic acid molecules. Specifically, SMASH fragments are composed of randomly ligated DNA segments. Random ligation in this instance implies that any segment has an equal probability of being directly ligated to any other segment.

As used herein, the term "sequencing adaptor" refers to oligos bound to the 5' and 3' end of each DNA fragment in a sequencing library. Adaptors contain platform-dependent sequences that allow amplification of the fragment as well as sequences for priming the sequencing reaction. Adaptors may also contain unique sequences, known as barcodes or indexes, which are used to identify the sample origin of each fragment. The adaptor may contain regions which are used as primer binding sites for other enzymatic reactions, such as amplification by PCR.

As used herein, the term "barcode", also known as an "index," refers to a unique DNA sequence within a sequencing adaptor used to identify the sample of origin for each fragment.

As used herein, the term "multiplex" refers to assigning a barcode to each mixture of fragments from a single genomic source, pooling or otherwise mixing multiple mixtures of fragments, sequencing the entire collection of mixtures in a single sequencing run and subsequently sorting and identifying the genomic origin of each read by its barcode sequence.

As used herein, "substantially the same" sequences have at least about 80% sequence identity or complementarity, respectively, to a nucleotide sequence. Substantially the same sequences or may have at least about 95%, 96%, 97%, 98%, 99% or 100% sequence identity or complementarity, respectively.

As used herein, the term "substantially unique primers" refers to a plurality of primers, wherein each primer comprises a tag, and wherein at least 50% of the tags of the plurality of primers are unique. Preferably, the tags are at least 60%, 70%, 80%, 90%, or 100% unique tags.

As used herein, the term "substantially unique tags" refers to tags in a plurality of tags, wherein at least 50% of the tags of the plurality are unique to the plurality of tags. Preferably, substantially unique tags will be at least 60%, 70%, 80%, 90%, or 100% unique tags.

As used herein, the term "tag" refers to a nucleic acid having a sequence no greater than 1000 nucleotides and no less than two that may be covalently attached to a nucleic acid molecule or reagent molecule. A tag may comprise a part of an adaptor or a primer.

As used herein, a "tagged nucleic acid molecule" refers to a nucleic acid molecule which is covalently attached to a "tag."

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

All publications and other references mentioned herein are incorporated by reference in their entirety, as if each individual publication or reference were specifically and individually indicated to be incorporated by reference. Publications and references cited herein are not admitted to be prior art.

This invention will be better understood by reference to the Experimental Details which follow, but those skilled in the art will readily appreciate that the specific experiments detailed are only illustrative of the invention as defined in the claims which follow thereafter.

Experimental Details

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only.

Methods—DNA Materials

DNA samples used in this example were from two sources. One source of the genomic DNA was extracted from SKBR3, a human breast cancer cell line. The other was extracted from blood from two families, which are from the Simons Simplex Collection (SSC) with samples and data from the mother, the father, the proband, and an unaffected sibling (Fischbach and Lord, 2010).

Methods—SMASH Protocol

The amount of genomic DNA required for SMASH is flexible. Three different genomic DNA inputs—200 ng, 500 ng and 1 µg—were tested and successfully constructed high quality libraries for all three conditions. In this example, 1 µg of DNA was used as starting material from all the samples. DNA was diluted in 1×Tris buffer (10 mM Tris-Cl, pH 8.5) to a final volume of 75 µl, and transferred to microtubes (Covaris). The Covaris E210 AFA instrument (Covaris) was used to shear the genomic DNA into segments with average length of 100 bp according to the manufacturer's manual. DNA segments were further cut by CvikI-1 (NEB) and NlaIII (NEB) in 1× CutSmart buffer in a final volume of 90 µl, which was incubated at 37° C. for 1 hr. After enzyme digestion, the volume of solution was reduced to about 30 µl by Savant SpeedVac (Thermo Scientific). DNA segments longer than 100 bp were removed as follows: adding 2.5× volume of AMPure XP beads (Beckman Coulter), mixing well, incubating at room temperature (RT) for 5 min, and collecting supernatant. The supernatant was the purified by QIAquick nucleotide removal kit (Qiagen) following manufacturer's instructions. DNA segments were eluted in 30 µl $H_2O$. The average length of DNA segments was 40-50 bp as determined by the Bioanalyzer 2100 (Agilent Technologies). These DNA segments were end-repaired by T4 DNA polymerase (NEB), DNA polymerase I (large Klenow fragment, NEB) and T4 Polynucleotide Kinase (NEB) at RT for 30 min. The polished DNA segments were purified by QIAquick nucleotide removal kit (Qiagen) with 30 µl $H_2O$ elution. The short DNA segments were randomly ligated to form longer fragments of chimeric DNA with the quick ligation kit (NEB) at RT for 15 min. The long DNA chimeric fragments were purified using 1.6× AMPure XP beads, and end-repaired as earlier. A single 'A' nucleotide was added to the 3' ends of the polished DNA fragments by Klenow fragment (3"->5" exo, NEB) at 37° C. for 30 min. After purification by 1.6×AMPure XP beads, barcoded sequencing adapters [Iossifov et al. 2012, Neuron] were ligated to the DNA fragments by quick ligation. This allowed for multiplex samples on sequencing lanes. DNA fragments were again purified by 1.6×AMPure XP beads, and eluted in 50 µl $H_2O$. This size selection step was carried out to enrich for DNA fragments within the ideal Illumina sequencing length range of 300-700 bp. First, 0.6× (30 µl) AMPure XP beads was added into 50 µl of purified DNA. After incubation at RT for 5 min, supernatant was collected. 8 µl (0.16× the original 50 µl) of AMPure XP beads was added, and mixed well with the supernatant. This mixture was incubated at RT for 5 min. After 2 washes with 180 µl of 80% ethanol, DNA fragments were eluted in 30 µl H2O. The final 8 cycles of PCR amplification were carried out on this DNA using Illumina sequencing adapters in 1× Phusion® High-Fidelity PCR Master Mix with HF Buffer (NEB). DNA libraries were quantitated on the Bioanalyzer and diluted to a concentration of 10 nM. Sequencing was performed on the HiSeq 2000 (paired-end 100 bp, Illumina) for libraries prepared from SSC families and the NextSeq 500 (paired-end 150 bp, Illumina) for libraries prepared from the SKBR3 cell line.

Methods—Determining Maps

WGS and SMASH data were mapped to the GATE b37 genome. For WGS, read 1 was clipped to 76 bp, mapped using Bowtie1, and duplicates were then filtered using Samtools. For SMASH (after the mapping procedure described below), the multiple-MAM signature of each read pair was used to filter duplicates. For both methods, only unique mappings to chromosomes 1-22, X and Y only were bin-counted.

To prepare for mapping SMASH data, the sparseMEM package (Khan et al., 2009) was modified to increase the maximum genome size from $2.147 \times 10^9$ bases to an essentially unlimited value, and the sparse functionality was removed to increase program speed and decrease complexity. Features were added to 1) save the various suffix array index structures to disk; 2) to read them in for subsequent runs using memory-mapping; 3) to distribute reads to the parallel query threads to avoid multiple parsing of the input; and 4) to read several query files in parallel. Options were also added to read input data from FASTQ and SAM files, to output mappings and non-mapping reads in SAM and custom binary formats, and to simultaneously map to the genome and its reverse complement to avoid a Maximal Exact Match (MEM) pruning step. The resulting software package is called longMEM for its ability to handle longer genomes.

Using longMEM, we searched for Maximal Almost-unique Matches (MAMs), which are maximally extended subsequences in query reads that match uniquely within the reference and its reverse complement, but may be repeated in the query. For query reads of length Q and a reference of length R, we find all MAMs in the query in $O(Q^*(Q \log(R)))$ time using the reference, the suffix array, its inverse and an LCP (Longest Common Prefix) table.

Most segments composing SMASH reads result in MAMs that are suitable for copy number analysis. The exceptions are segments that are not present in the reference due to blocking read errors or mutation, and those that are too short to be uniquely mapped to their origin. In addition to acceptable MAMs, junctions between adjacent segments in SMASH sometimes result in one or more MEMs being found. If unique in the reference, these are reported as spurious MAMs.

MAMs were filtered by discarding MAMs less than 20 bp and not at least 4 bases longer than required for uniqueness. Assuming a random genome and ignoring the usage of restriction enzymes, this naively reduced spurious MAM contamination by a factor of $4^4$. Because the mode for minimum mappable length in the genome is 18 bp, the average is 29 bp and segments are typically 40 bp in length, it is believed that the filter did not greatly reduce the number of reported legitimate MAMs. An additional filter turns our MAMs into MUMs by ensuring that no retained MAMs in a read pair map within 10,000 bp of another, which avoids double-counting of segments containing indels or SNPs as well as MAMs read from both ends in short chimeric fragments.

Methods—Binning, Normalization, and Copy Number

Chromosomes 1-22, the X and the Y were divided into 50,000, 100,000 and 500,000 WGS-optimized bins by mapping every 50-mer in the reference with Bowtie1 and adjusting bin boundaries so that each bin had the same number of uniquely mapped reads assigned to it (±1).

An equal number of mappings were assigned from SSC WGS and SMASH data to bins and added one count to each total. Counts were normalized to set the mean of all autosome bins to 1, then LOESS was performed on the normalized autosome to correct for GC site density. After bin-wise summation across samples, bad bins were selected based on upward copy number deviation from the chromosome median exceeding a MAD-based limit using a Bonferroni-corrected p value of 0.05.

SSC and SKBR3 mappings were sampled at 20, 50, 100 and up to 1000 (if available) mappings per bin and assigned them to bins, in this instance excluding bins marked as bad. Sample counts were divided at low maps per bin on a bin-wise basis by a non-related male reference sample, using the highest maps per bin. The ratio data was normalized and GC-corrected, then segmented using CBS with the minimum segment length and alpha parameters set to 3 and 0.02, respectively. Segmented profiles were adjusted by varying the overall scale and offset within expected bounds to find the best quantal fit.

Methods—WGS and SMASH Quantification and Comparison

SSC sample signal to noise was defined for SMASH and WGS as the autosome minus the X chromosome median un-quantized ratio, divided by its measured MAD-based noise for male samples using a female reference sample (when performing reference normalization). We also counted the quantized and rounded segmented autosome bin values different than 2 to place an upper bound on deviation from the SSC diploid expectation. WGS and SMASH concordance were assessed for SSC and SKBR3 data by plotting the lengths of bin runs on histograms for un-quantized segmented ratios that differed by more than 0.2.

Example 1. Overview of SMASH

The protocol for SMASH (see also "Methods—Smash protocol," above) is illustrated in FIG. 1. To obtain SMASH tags, first genomic DNA was mechanically sheared by sonication, then cut with two restriction endonucleases. The ideal size fraction is obtained using bead purification (see also "Methods—Smash protocol," above) to enrich for the target size range of 40 bp (FIG. 1). To generate the long chimeric DNAs, the SMASH tags were end-repaired and then ligated. A second fragmentation step may optionally be performed to eliminate long (>1 kb) chimeric molecules, and DNA fragments in the proper size range (300-700 bp) are purified. Barcoded sequencing adaptors are then attached to the molecules, creating libraries that can be multiplexed on a single sequencing lane. Alternatively, long chimeric DNAs can be formed by ligation of end-repaired SMASH segments, followed by attachment of barcoded sequencing adaptors to the fragments and finally selection of DNA fragments in the optimal size range for sequencing (300-700 bp) by bead purification. The protocol is robust and reproducible, typically generating libraries with nearly identical distributions of segment and fragment lengths (FIG. 5). While the SMASH library may contain a low amount of segments and fragments outside of the desired size range, these contaminants are inconsequential and do not affect the copy number variation determination in any way.

To obtain mapping information from the chimeric reads, an algorithm and a set of heuristics was applied, described briefly here (see FIG. 2 and Methods for additional details). sparseMEM (Khan et al., 2009), a program that uses suffix arrays to quickly determine all maximal almost-unique matches (or MAMs) between a NGS read and the reference genome was adapted. The mappings of a read pair provide a unique signature for each SMASH read, allowing easy identification as well as removal of PCR duplicates. A heuristic was used that identifies distinct unambiguous matches (or 'maps') spanned by the read pair. The parameters of the heuristic have been calibrated to maximize quality of the copy number data by balancing the number of maps per read against the quality of the map assignment.

The copy number detection protocol of the present invention is based on map-counting methods, and it requires that bin boundaries were first determined to partition the genome. 'Bins of expected uniform density,' first used for single cell genome copy number determination (Navin et al., 2011), are employed. Boundaries are chosen such that each bin contains the same expected number of maps when sequencing the reference genome with exhaustive coverage and perfect reads. SMASH and WGS have different distributions of expected map densities due to variation in map lengths. Bin boundaries were chosen suitable for WGS, and map the WGS reads in single-end mode using the first 76 bp. For each sample, the number of maps that fall within each bin was counted and bin counts were adjusted for GC bias by LOESS normalization.

Both WGS and SMASH have distinct patterns of systematic noise that extend beyond the gross-scale corrections of GC adjustment. This is evidenced by strong correlation between independent samples. Moreover, this systematic noise is trendy, leading to high autocorrelation, and so is likely to trigger false-positive copy number events. This error was corrected by choosing one sample as a reference, then dividing all remaining sample data by that reference. The resulting copy number segmentation typically results in segment means that are low integer fractions, reflecting copy number in the sample. With sufficient samples (and using multiple reference samples), it is possible to determine absolute copy number. For analysis of bin count data, the standard method of circular binary segmentation was used (Olshen et al., 2004).

Example 2. Optimizing Pipeline Parameters

To measure performance precisely and choose parameters for pipeline processing, the signal in bins was compared on the X chromosome to those on autosomes in male subjects. Also calculated are 1) the median average deviation (MAD) of bins to measure the magnitude of the noise, and 2) the autocorrelation as a measure of trendiness in the data, an important risk factor for segmentation error. Signal to noise ("S/N") was calculated as the difference in the medians of the autosome and X-chromosome, divided by the square root of the sum of the squares of the MADs. These statistics were used to evaluate reference normalization and mapping algorithms, and then to compare WGS to SMASH (Table 1).

First, the utility of applying reference normalization ("ref norm," Table 1) was considered. Dividing the GC-adjusted bin ratios by a standard sample bin ratio greatly improved performance for both WGS and SMASH (rows 1 through 4). Namely, reference normalization decreases "autocorrelation" up to ten fold while increasing "signal to noise".

unique matches (see also "Methods—Determining maps"). A minimum match length, L, as the first parameter is required. For the data shown here, L is 20 bp. To avoid false maps that arise by chimerism, a second rule is required, namely a MAM of length M contains a substring of length M-K that maps uniquely to the genome. Many combinations of L and K were examined, and their performance was measured on an identical set of SMASH reads, with fixed bin boundaries. Only the results for rules 20:0, 20:4 and 20:8 (Table 1 rows 5-7) are shown. Despite having far fewer maps ("maps per bin"), the 20:4 rule is superior to the 20:0 rule as judged by "signal to noise". Many of the 20:0 maps must be false. This false mapping can be attributed to chimerism at fragment boundaries. On the other hand, the 20:4 rule is superior to the 20:8 rule as judged by a slightly degraded

TABLE 1

Table 1. Reference normalization and mapping rules.

| rule | type | ref norm | number of bins | maps per bin | auto correlation | autosome median | x chrom median | autosome MAD | x chrom MAD | signal to noise |
|---|---|---|---|---|---|---|---|---|---|---|
| — | wgs | yes | 100000 | 50 | 0.012 | 2.008 | 1.032 | 0.194 | 0.138 | 4.102 |
| — | wgs | no | 100000 | 50 | 0.075 | 2.012 | 1.040 | 0.202 | 0.139 | 3.959 |
| 20.4 | smash | yes | 100000 | 50 | 0.011 | 2.010 | 1.071 | 0.196 | 0.146 | 3.833 |
| 20.4 | smash | no | 100000 | 50 | 0.109 | 2.015 | 1.055 | 0.212 | 0.148 | 3.718 |
| 20.0 | smash | yes | 100000 | 117.28 | 0.010 | 2.010 | 1.419 | 0.137 | 0.129 | 3.148 |
| 20.4 | smash | yes | 100000 | 63.98 | 0.012 | 2.006 | 1.062 | 0.176 | 0.129 | 4.333 |
| 20.8 | smash | yes | 100000 | 53.09 | 0.013 | 2.008 | 1.034 | 0.192 | 0.140 | 4.094 |

In Table 1 auto-correlation, medians and median absolute deviation (MADs) for the autosome and X chromosomes in males, and the resultant signal-to-noise, is computed. The first four entries compare WGS and SMASH for the same bin resolution (100,000) and the same average number of maps per bin (50). Results with and without normalizing by a reference sample are shown. SMASH and WGS have similar performance and both methods reduce autocorrelation by reference normalization while maintaining signal-to-noise. The lower three entries compare SMASH performance using different rules for selecting valid maps (see text). Each SMASH instance operates on the same number of reads with the most lax rule (20,0) generating 117 maps per bin and the strictest rule (20,8) generating 53 maps per bin. The best signal-to-noise is obtained with the 20,4 rule.

Next we established a two-part, two parameter (L,K) rule for accepting the map of a substring from a SMASH read to the reference genome (see FIG. 2, panel A). First, all substrings in a read were found that occur just once in the reference genome and such that the match cannot be extended. These are called "MAMs," for maximal almost- "signal to noise" that can be attributed to increased sampling error due to reduced coverage. Therefore, the 20:4 rule is employed throughout.

Example 3. Comparing WGS to SMASH Profiles Under Optimized Pipeline Parameters

The performance of WGS and SMASH was compared using autosomes and X-chromosomes as described above. Different total numbers of bins (from 50,000 to 500,000), different mean numbers of maps per bin (20, 50 and 100), collecting statistics for signal-to-noise and autocorrelation were considered, among other factors. The two methods have very similar performance characteristics (Table 2). WGS, map for map, slightly outperforms SMASH. When bin boundaries were chosen such that the reference sample has the same number of maps in each bin, the signal-to-noise ratio improves for both SMASH and WGS, and the difference between them narrows substantially (Supplementary Table 1).

TABLE 2

Table 2. WGS and SMASH by number of bins and maps.

| type | # of bins | maps per bin | autosome auto-correlation | autosome median | X-chrom median | autosome MAD | X-chrom MAD | signal to noise |
|---|---|---|---|---|---|---|---|---|
| smash | 50000 | 20 | −0.002 | 2.032 | 1.111 | 0.297 | 0.218 | 2.497 |
| wgs | 50000 | 20 | 0.000 | 2.031 | 1.072 | 0.295 | 0.208 | 2.659 |
| smash | 50000 | 50 | 0.006 | 2.009 | 1.068 | 0.194 | 0.140 | 3.933 |
| wgs | 50000 | 50 | 0.000 | 2.007 | 1.032 | 0.191 | 0.135 | 4.173 |
| smash | 50000 | 100 | 0.009 | 2.002 | 1.056 | 0.141 | 0.100 | 5.487 |
| wgs | 50000 | 100 | 0.008 | 2.002 | 1.019 | 0.138 | 0.095 | 5.861 |
| smash | 100000 | 20 | 0.004 | 2.033 | 1.108 | 0.298 | 0.224 | 2.481 |
| wgs | 100000 | 20 | 0.003 | 2.031 | 1.070 | 0.297 | 0.212 | 2.633 |
| smash | 100000 | 50 | 0.011 | 2.010 | 1.071 | 0.196 | 0.146 | 3.833 |
| wgs | 100000 | 50 | 0.012 | 2.008 | 1.032 | 0.194 | 0.138 | 4.102 |

TABLE 2-continued

Table 2. WGS and SMASH by number of bins and maps.

| type | # of bins | maps per bin | autosome auto-correlation | autosome median | X-chrom median | autosome MAD | X-chrom MAD | signal to noise |
|---|---|---|---|---|---|---|---|---|
| smash | 100000 | 100 | 0.019 | 2.003 | 1.056 | 0.145 | 0.105 | 5.289 |
| wgs | 100000 | 100 | 0.019 | 2.002 | 1.021 | 0.143 | 0.099 | 5.633 |
| smash | 500000 | 20 | 0.008 | 2.033 | 1.109 | 0.318 | 0.233 | 2.342 |
| wgs | 500000 | 20 | 0.010 | 2.033 | 1.075 | 0.315 | 0.221 | 2.492 |
| smash | 500000 | 50 | 0.016 | 2.013 | 1.073 | 0.225 | 0.159 | 3.410 |
| wgs | 500000 | 50 | 0.019 | 2.011 | 1.037 | 0.220 | 0.150 | 3.656 |
| smash | 500000 | 100 | 0.024 | 2.004 | 1.059 | 0.181 | 0.122 | 4.319 |
| wgs | 500000 | 100 | 0.029 | 2.003 | 1.023 | 0.177 | 0.114 | 4.649 |

The same performance statistics as in Table 1, comparing SMASH and WGS over a range of resolutions (50K, 100K, and 500K) and coverage (20, 50, and 100 maps per bin) are computed in Table 2.

SUPPLEMENTARY TABLE 1

Supplementary Table 1. Empirical bin boundaries.

| type | # of bins | maps per bin | autosome auto-correlation | autosome median | X-chrom median | autosome MAD | X-chrom MAD | signal to noise | S/N from Table 2 |
|---|---|---|---|---|---|---|---|---|---|
| smash | 50000 | 20 | 0.006 | 2.020 | 1.120 | 0.295 | 0.161 | 2.679 | 2.497 |
| wgs | 50000 | 20 | 0.002 | 2.021 | 1.079 | 0.296 | 0.160 | 2.800 | 2.659 |
| smash | 50000 | 50 | 0.009 | 2.005 | 1.074 | 0.193 | 0.106 | 4.234 | 3.933 |
| wgs | 50000 | 50 | 0.008 | 2.005 | 1.036 | 0.192 | 0.099 | 4.480 | 4.173 |
| smash | 50000 | 100 | 0.015 | 2.002 | 1.060 | 0.140 | 0.077 | 5.886 | 5.487 |
| wgs | 50000 | 100 | 0.013 | 2.002 | 1.026 | 0.140 | 0.074 | 6.149 | 5.861 |
| smash | 100000 | 20 | 0.003 | 2.020 | 1.116 | 0.298 | 0.159 | 2.681 | 2.481 |
| wgs | 100000 | 20 | 0.005 | 2.020 | 1.078 | 0.299 | 0.157 | 2.788 | 2.633 |
| smash | 100000 | 50 | 0.016 | 2.006 | 1.074 | 0.197 | 0.108 | 4.148 | 3.833 |
| wgs | 100000 | 50 | 0.008 | 2.005 | 1.039 | 0.197 | 0.102 | 4.368 | 4.102 |
| smash | 100000 | 100 | 0.024 | 2.002 | 1.061 | 0.146 | 0.078 | 5.697 | 5.289 |
| wgs | 100000 | 100 | 0.017 | 2.002 | 1.024 | 0.145 | 0.077 | 5.979 | 5.633 |
| smash | 500000 | 20 | 0.009 | 2.021 | 1.113 | 0.317 | 0.170 | 2.524 | 2.342 |
| wgs | 500000 | 20 | 0.008 | 2.020 | 1.078 | 0.315 | 0.163 | 2.657 | 2.492 |
| smash | 500000 | 50 | 0.018 | 2.006 | 1.075 | 0.225 | 0.116 | 3.677 | 3.410 |
| wgs | 500000 | 50 | 0.017 | 2.005 | 1.037 | 0.222 | 0.109 | 3.906 | 3.656 |
| smash | 500000 | 100 | 0.028 | 2.001 | 1.060 | 0.182 | 0.090 | 4.622 | 4.319 |
| wgs | 500000 | 100 | 0.026 | 2.001 | 1.025 | 0.179 | 0.084 | 4.939 | 4.649 |

Note that as the number of bins increases, the signal-to-noise ratio diminishes: from 5.6 at 50K bins to 4.0 at 500K bins for SMASH. Similar degradation of signal occurs for WGS. It was hypothesized that this was the result of using the same total number of reference maps for normalization, independent of the number of bins. Therefore, as the number of bins increases, the number of reference maps per bin diminishes, increasing the variance of the normalized ratio. To test if this was the cause, reference normalization was performed—this time matching the total number of reference maps to the total number of sample maps. There was virtually no degradation of signal-to-noise ratio as the bin number increased (Supplementary Table 2).

The computations of Table 2 are repeated, but instead of bins of uniform expectation, bins of uniform observation of a reference are used. The bin boundaries are defined empirically: establishing bins with the same number of maps as determined empirically. The signal-to-noise is improved over the results in Table 2 ("S/N from Table 2"), with little change to the autocorrelation.

SUPPLEMENTARY TABLE 2

Supplementary Table 2. Matching reference and sample coverage.

| type | # of bins | maps per bin | autosome auto-correlation | autosome median | X-chrom median | autosome MAD | X-chrom MAD | signal to noise |
|---|---|---|---|---|---|---|---|---|
| smash | 50000 | 20 | 0.002 | 2.027 | 1.112 | 0.416 | 0.272 | 1.8401 |
| smash | 100000 | 20 | 0.004 | 2.028 | 1.122 | 0.415 | 0.279 | 1.812 |
| smash | 500000 | 20 | 0.003 | 2.025 | 1.112 | 0.417 | 0.279 | 1.819 |
| smash | 50000 | 50 | 0.004 | 2.019 | 1.075 | 0.270 | 0.176 | 2.928 |
| smash | 100000 | 50 | 0.005 | 2.018 | 1.077 | 0.269 | 0.180 | 2.907 |
| smash | 500000 | 50 | 0.011 | 2.019 | 1.076 | 0.271 | 0.178 | 2.908 |
| smash | 50000 | 100 | 0.005 | 2.003 | 1.058 | 0.190 | 0.124 | 4.160 |
| smash | 100000 | 100 | 0.009 | 2.005 | 1.061 | 0.190 | 0.126 | 4.130 |
| smash | 500000 | 100 | 0.021 | 2.005 | 1.059 | 0.194 | 0.128 | 4.073 |
| wgs | 50000 | 20 | 0.004 | 2.034 | 1.080 | 0.413 | 0.261 | 1.953 |

SUPPLEMENTARY TABLE 2-continued

Supplementary Table 2. Matching reference and sample coverage.

| type | # of bins | maps per bin | autosome auto-correlation | autosome median | X-chrom median | autosome MAD | X-chrom MAD | signal to noise |
|---|---|---|---|---|---|---|---|---|
| wgs | 100000 | 20 | 0.001 | 2.032 | 1.075 | 0.414 | 0.261 | 1.955 |
| wgs | 500000 | 20 | 0.003 | 2.030 | 1.078 | 0.413 | 0.263 | 1.944 |
| wgs | 50000 | 50 | 0.003 | 2.017 | 1.036 | 0.267 | 0.164 | 3.132 |
| wgs | 100000 | 50 | 0.006 | 2.016 | 1.039 | 0.266 | 0.168 | 3.111 |
| wgs | 500000 | 50 | 0.012 | 2.016 | 1.040 | 0.267 | 0.168 | 3.095 |
| wgs | 50000 | 100 | 0.008 | 2.003 | 1.017 | 0.189 | 0.114 | 4.452 |
| wgs | 100000 | 100 | 0.011 | 2.003 | 1.022 | 0.189 | 0.118 | 4.400 |
| wgs | 500000 | 100 | 0.025 | 2.003 | 1.024 | 0.189 | 0.119 | 4.385 |

Performance statistics as in Table 2 are computed. In this table, however, the same number of maps for both the sample and the reference are used for each choice of bin resolution (50K, 100K, 500K) and for each map coverage (20, 50 and 100 reads per bin). When the number of maps are equalized between sample and reference, the signal to noise is largely insensitive to the bin resolution and depends strongly on the map coverage for both WGS and SMASH, indicating that only the depth of coverage limits resolution.

Figure 3A:
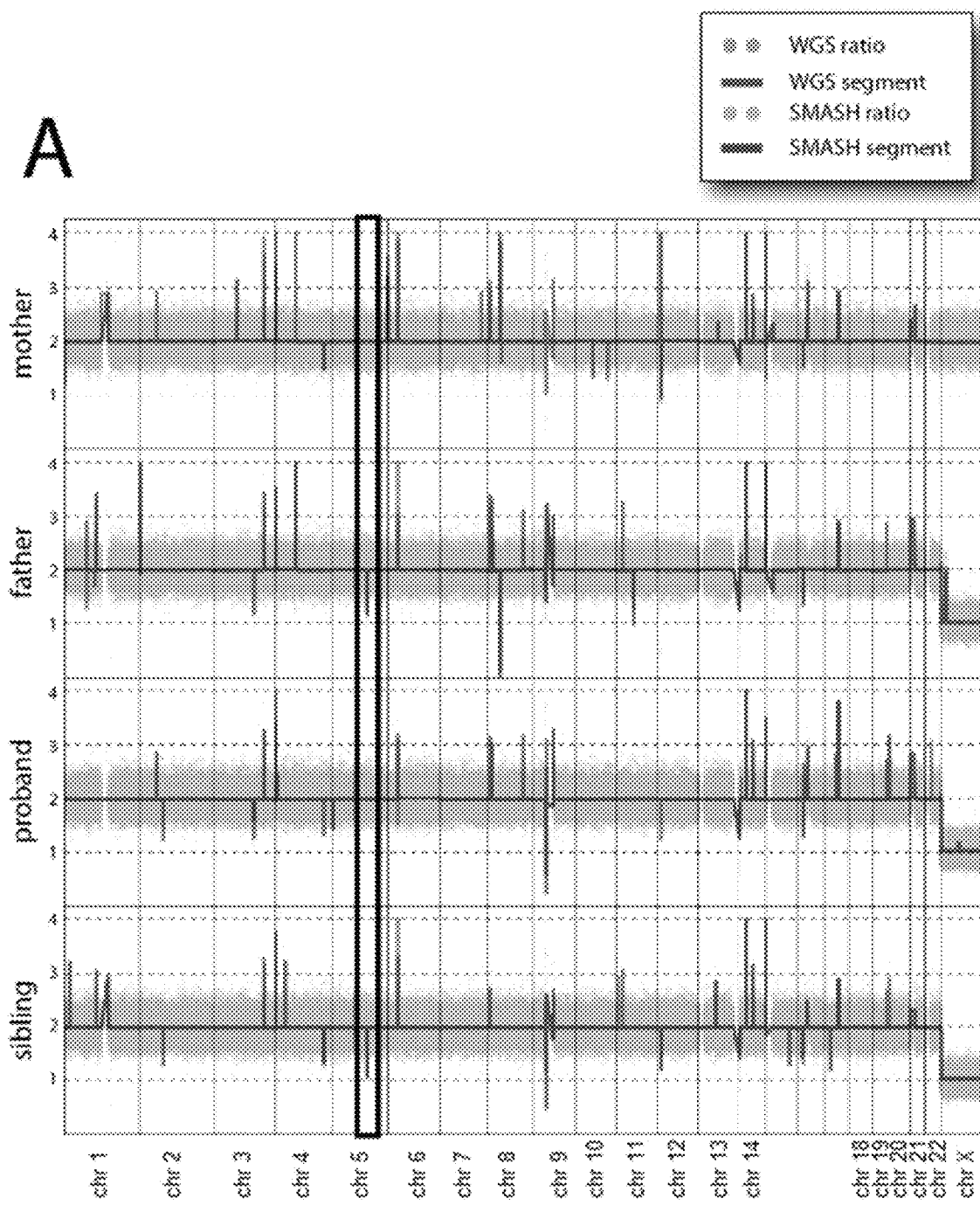

Finally, the actual profiles of samples using SMASH and WGS were compared. Bins optimized for WGS and the map selection rules discussed above were used. Genomic DNAs from two families using reference normalization (FIG. 3) and one cancer cell line without reference normalization (FIG. 4) were analyzed. For comparison, both WGS and SMASH were down-sampled to an equal number of maps. Across all scales of genome resolution—whether looking at normalized bin counts or segmented data—the profiles from the two methods look very similar. In both figures, 10 million maps distributed into 100,000 bins are shown. Parental transmission patterns appeared largely Mendelian (FIG. 3A). This is illustrated clearly in FIG. 3B, which zooms to show the transmission of a deletion from the father to an unaffected sibling. While the global segmentation patterns generated by SMASH and WGS are not completely identical, much of the variation has to do with segmentation itself. When considering bin concordance, WGS and SMASH are exceedingly similar (FIG. 3C).

Figure 4C:
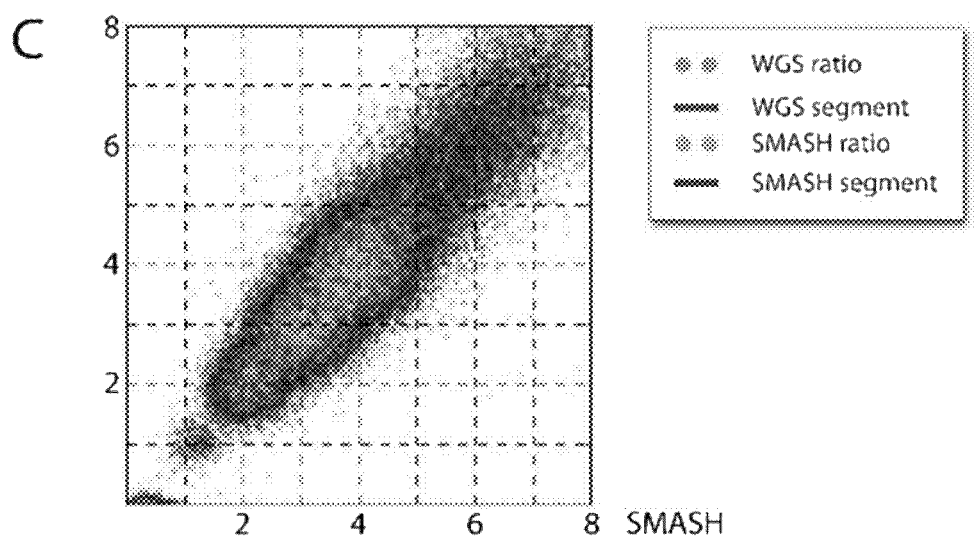

Both WGS and SMASH yielded approximately the same integer-valued copy number profile for the cancer cell line SKBR3 (FIG. 4A). The copy number profiles are well matched to integer states. To illustrate the concordance between the data, a chromosome with extensive genomic copy number variation is shown in greater detail (FIG. 4B). Again, the bin-for-bin LOESS adjusted ratios are largely concordant (FIG. 4C).

Example 4. An Alternate Fractionation Protocol for SMASH

All of the above data derive from a version of SMASH that combines sonication and restriction endonuclease (RE) cleavage. A version that did not depend on either of those methods for genomic fragmentation, and that might be more amenable to ideal segment length distribution and randomness of SMASH maps was desirable. For this purpose NEBNext dsDNA Fragmentase (NEB) was used. NEBNext dsDNA Fragmentase (NEB) is a combination of enzymes that randomly generates nicks on dsDNA, then cuts the DNA strand opposite the nick to produce dsDNA breaks. Using recommended conditions, segment lengths with a tighter size distribution and somewhat shorter than those obtained by sonication and RE cleavage were readily obtained. Ligation of the segments and size-selection of the fragments to an optimal length for sequencing was readily accomplished (FIG. 6). This method was then compared to our initial protocol on genomic DNA from the cancer cell line SKBR3, without normalization. The copy number profiles generated by the two methods were virtually identical (FIG. 7). The average number of maps per read increases from greater than four to more than six with the fragmentase method. The improvement is likely due to more precise sizing in this protocol. The detailed SMASH library preparation using the alternative protocol is outlined below:

Step 1—dsDNA Fragmentation.

Set up the fragmentation reaction as follows:

| Component | stock conc. | unit | vol. (µl) |
|---|---|---|---|
| Genomic DNA (200 ng-1 µg) | varies | ng/µl | x |
| Fragmentase reaction Buffer v2 | 10 | x | 1 |
| MgCl$_2$ | 200 | mM | 0.5 |
| dsDNA Fragmentase (NEB, M0348L) | | | 1 |
| H$_2$O | | | y |
| Total | | | 10 |

Incubate tubes in a thermal cycler for 10 minutes at 37° C., then put the tubes on ice.

Step 2—End-Repair.

Add the following reagents into the same tube(s) as step 1:

| Component | stock conc. | unit | vol. (µl) |
|---|---|---|---|
| ATP (NEB, P0756L) | 10 | mM | 2 |
| dNTPs (Roche 11814362001) | 10 | mM | 1 |
| T4 DNA Polymerase (NEB M0203L) | 3 | U/ul | 1 |
| Klenow Polymerase, large fragment (NEB M0210L) | 5 | U/µl | 0.5 |
| T4 PNK (NEB M0201L) | 10 | U/µl | 1 |
| H$_2$O | | | 4.5 |
| Fragmented DNA | 25 | ng/ul | 10 |
| total | | | 20 |

Incubate the sample in a thermal cycler for 30 minutes at 20° C. Size select with AMPure XP beads (2.5×), mix well, incubate at RT for 5 min, collect supernatant, purify by nucleotide removal kit (Qiagen), and elute with 30 µl H$_2$O. Take 1 µl aliquot for Bioanalyzer.

Step 3—Self Random Ligation.

Prepare the following reaction mix in a new 0.2 ml PCR tube:

| Component | stock conc. | unit | vol. (μl) |
|---|---|---|---|
| DNA Quick Ligase Buffer | 2 | x | 29 |
| Quick DNA Ligase (NEB, M2200L) | | | 1.5 |
| Eluted DNA from step 2 | | | 27.5 |
| Total | | | 58 |

Incubate in a thermal cycler at 25° C. for 15 min. Purify by AMPure XP bead (1.6×, 92.8 ul bead), wash twice with 180 μl 80% ethanol, air dry, elute by 25 ul H2O, add to new PCR tube. Take 1 μl aliquot for Bioanalyzer.

Step 4—Second End-Repair.

Prepare the following reaction mix in a new 0.2 ml nuclease-free PCR tube:

| Component | vol. (μl) |
|---|---|
| T4 DNA lig buffer w/10 mM ATP (w/DTT, B0202) 10X | 3 |
| dNTPs (Roche, 11814362001, or 04638956001) 10 mM | 1 |
| T4 DNA Polymerase (NEB M0203L) 3 U/μl | 1 |
| T4 PNK (NEB M0201L) 10 U/μl | 1 |
| Klenow Polymerase, large fragment (NEB M0210L) 5 U/μl | 0.5 |
| Size-selected DNA from step 3 | 23.5 |
| Total | 30 |

Incubate the sample on a thermal cycler for 30 minutes at 20° C. Purify with AMPure XP beads (1.6×, 48 μl), RT for 10 min, wash twice with 180 μl of 80% ethanol, elute by 21 ul H$_2$O.

Step 5—Adenylate 3' Ends.

Prepare the following reaction mix in a new 0.2 ml nuclease-free PCR tube:

| Component | vol. (μl) |
|---|---|
| Eluted DNA from step 4 | 20 |
| NEBuffer #2 10X | 2.5 |
| dATP (Roche, 100 mM, 11934511001) 2 mM | 1 |
| Klenow fragment 3'_-5'_ exo (NEB M0212L) 5 U/μl | 1.5 |
| Total | 25 |

Incubate the sample in a thermal cycler for 30 minutes at 37° C. Purify with AMPure XP bead (1.6×, 40 μl), incubate at RT for 10 min, wash twice with 180 μl of 80% ethanol×2, elute with 14 μl H$_2$O.

Step 6—Ligate with Adapters and Size Select with AMPure XP Beads.

Prepare the following reaction mix in a new 0.2 ml nuclease-free PCR tube:

| Component | stock conc. | unit | Vol. (μl) |
|---|---|---|---|
| Product from step 5 | | | 13 |
| DNA Quick Ligase Buffer | 2 | x | 15 |
| Barcoded adapters | 10 | uM | 1 |
| Quick DNA Ligase (NEB, M2200L) | | U/ul | 1 |
| Total | | | 30 |

Incubate at 25° C. for 10 min. Purify by AMPure bead (1.6×, 48 μl), wash twice with 80% ethanol, elute with 50 μl H$_2$O. Size select with AMPure beads (0.6×, 30 ul), mix well and incubate at RT for 10 min, collect supernatant, add AMPure beads (0.16×, 8 μl), mix well and incubate at RT for 10 min, wash twice with 180 μl 80% ethanol, and elute with 16 μl H$_2$O.

Step 7—Enrichment PCR.

Set up PCR reaction as follows:

| Component | stock conc. | unit | vol. (μl) |
|---|---|---|---|
| Phusion mm (M0531L) | 2 | x | 20 |
| DNA from step 6 | | | 15 |
| PE5 & PE7 primers | 5 | μM (ea.) | 2 |
| H$_2$O | | | 3 |
| Total | | | 40 |

Amplify under following conditions: denature at 98° C. for 30 sec; perform 8 cycles of denaturing at 98° C. for 5 sec, primer annealing at 65'C for seconds, and template extension at 72° C. for 30 sec; final extension at 72° C. for 10 min. Purify by AMPure beads (0.9×, 36 μl), wash twice with 180 μl 80% ethanol, elute with 20 μl H$_2$O. Measure concentration by Nanodrop, take aliquot and dilute to 10 ng/μl for Bioanalyzer. The SMASH DNA library is now ready for sequencing.

Thus, the two steps of sonication and the restriction enzyme digestion in the general protocol have been replaced by one step of fragmenation with dsDNA Fragmentase (NEB) in the alternative protocol. Accordingly, the first end-repair reaction is right after the fragmentation step—there is no longer any need for purification between these two steps. Additionally, all enzyme heat-killing steps have been eliminated in the alternative protocol because enzymes are adequately removed by bead purification. Ultimately, the overall time requirement for the SMASH library preparation has been reduced by approximately one hour using the alternative protocol.

DISCUSSION

Copy number variants (CNVs) underlie a significant amount of genetic diversity and disease. For example, Autism Spectrum Disorders (ASD) are highly influenced by genetic factors (Muhle et al., 2004; Rosenberg et al., 2009), and CNVs underlie a significant fraction of those diagnoses. Beyond ASD, copy number variants have been shown to play a role in multiple diseases, including congenital heart disease (Warburton et al., 2014), cancer (Stadler et al., 2012; Lockwood et al., 2007; Lu et al., 2011; Shlien and Malkin, 2009), schizophrenia (Szatkiewicz et al., 2014; Rees et al., 2014) and even in patients' responses to certain therapies (Willyard, 2015). CNVs can be detected by a number of means, including chromosomal microarray analysis (CMA)

and whole genome sequencing (WGS), but these approaches suffer from either limited resolution (CMA) or are highly expensive for routine screening (both CMA and WGS).

In obtaining copy number information from high throughput sequencing, SMASH has a clear advantage over standard WGS. Each read is packed with multiple independent mappings, increasing the information density per read and thereby lowering cost per sample. Map for map, SMASH is comparable in quality to WGS with respect to copy number profiling. There is, of course, an enormous amount of additional structural information present in WGS data that is missing in SMASH, such as breakpoints of copy number events, small scale indels, or inversions, as a consequence of the longer reads. However, discovery of such structural events by WGS typically requires much higher coverage than what is needed for copy number determination. For detecting CNVs several kb and larger, the choice should be driven by cost.

Significant effort was invested in optimizing the design of the SMASH protocol and algorithms. These include choice of restriction enzymes and sonication conditions, heuristics for selecting maps from SMASH reads and reference sample normalization. The result is a robust method that performs at parity with WGS on a map-for-map basis. Additional changes could further increase the number of useful SMASH maps per read—the fragmentation protocol is currently set for a median of ~40 bp segments, which is optimal using the existing mapping algorithm. However, variation in segment lengths is problematic, and this variation could be reduced by adjusting the fragmentation conditions and performing more stringent size selection. To this end, the use of DNAses to create random fragments with a mean of 35 bp has been explored to address the issue of segment length variation. With this somewhat simplified protocol, more maps per read with comparable resolution on a map-for-map basis were obtained in preliminary experiments.

For most of the analysis of maps, bin boundaries determined for WGS were used so that SMASH could be directly compared to WGS. However, the optimal bin boundaries were shown to be those derived empirically to yield uniform map counts (Supplementary Table 2). Furthermore, it is clear that increasing the reference coverage will improve signal to noise for all samples. A lower limit to the resolution that can be obtained has not yet been determined.

Advances in sequencing technology that reduce unit cost per base pair will likely be driven by increasing read lengths. For copy number inference from whole genome sequencing, this means a continued decline in the number of maps per base. However, SMASH, even with existing sequencers, can yield 4-6 times as many maps as standard WGS. On a machine that generates 300 million 150-bp paired-end reads for $1500, 60 million maps per sample for 30 samples at unit cost of $50 per sample and a resolution of ~10 kb can be obtained, not including the preparation costs for the libraries. However, using the same SMASH library, resolution and cost will be roughly linear to number of reads. Thus, SMASH can reduce the costs of testing in prenatal, pediatric and cancer genetics, allowing more patients to be tested at a lower cost and the resultant savings passed along to researchers and caregivers.

Ultimately, genomic copy number information can be used to test for prenatal, pediatric, developmental, psychological and autoimmune disorders, as well as susceptibility to disease. Examples of disorders and diseases which can be tested for using genomic copy number information include, but are not limited to, Autism Spectrum Disorders, schizophrenia, cancer and congenital heart disease. In addition to testing and diagnosis, copy number information may also be utilized to predict the likelihood of displaying or probability of inheriting a disease, syndrome or disorder. Finally, outside of the clinic SMASH may also prove to be a valuable tool for determining copy number variation in agriculturally important plants and crops.

REFERENCES

1. Alkan C, Kidd J M, Marques-Bonet T, Aksay G, Antonacci F, Hormozdiari F, Kitzman J O, Baker C, Malig M, Mutlu O, Sahinalp S C, Gibbs R A, Eichler E E. Personalized copy number and segmental duplication maps using next-generation sequencing. Nature genetics. 2009; 41(10):1061-7. doi: 10.1038/ng.437. PubMed PMID: 19718026; PubMed Central PMCID: PMC2875196.
2. Fishbach G D, Lord C. The Simons Simplex Collection: a resource for identification of autism genetic risk factors. Neuron. 2010; 68:192-195.
3. Khan Z, Bloom J S, Kruglyak L, Singh M. A practical algorithm for finding maximal exact matches in large sequence datasets using sparse suffix arrays. Bioinformatics. 2009; 25(13):1609-16. doi: 10.1093/bioinformatics/btp275. PubMed PMID: 19389736; PubMed Central PMCID: PMC2732316.
4. Levy D, Wigler M. Facilitated sequence counting and assembly by template mutagenesis. Proceedings of the National Academy of Sciences of the United States of America. 2014; 111 (43):E4632-7. doi: 10.1073/pnas.1416204111. PubMed PMID: 25313059; PubMed Central PMCID: PMC4217440.
5. Lockwood W W, Coe B P, Williams A C, MacAulay C, Lam W L. Whole genome tiling path array CGH analysis of segmental copy number alterations in cervical cancer cell lines. International journal of cancer Journal international du cancer. 2007; 120(2):436-43. doi: 10.1002/ijc.22335. PubMed PMID: 17096350.
6. Lu T P, Lai L C, Tsai M H, Chen P C, Hsu C P, Lee J M, Hsiao C K, Chuang E Y. Integrated analyses of copy number variations and gene expression in lung adenocarcinoma. PloS one. 2011; 6 (9):e24829. doi: 10.1371/journal.pone.0024829. PubMed PMID: 21935476; PubMed Central PMCID: PMC3173487.
7. Muhle R, Trentacoste S V, Rapin I. The genetics of autism. Pediatrics. 2004; 113 (5):e472-86. PubMed PMID: 15121991.
8. Navin N, Kendall J, Troge J, Andrews P, Rodgers L, McIndoo J, Cook K, Stepansky A, Levy D, Esposito D, Muthuswamy L, Krasnitz A, McCombie W R, Hicks J, Wigler M. Tumour evolution inferred by single-cell sequencing. Nature. 2011; 472(7341):90-4. doi: 10.1038/nature09807. PubMed PMID: 21399628; PubMed Central PMCID: PMC4504184.
9. Olshen A B, Venkatraman E S, Lucito R, Wigler M. Circular binary segmentation for the analysis of array-based DNA copy number data. Biostatistics. 2004; 5:557-572.
10. Rees E, Walters J T, Georgieva L, Isles A R, Chambert K D, Richards A L, Mahoney-Davies G, Legge S E, Moran J L, McCarroll S A, O'Donovan M C, Owen M J, Kirov G. Analysis of copy number variations at 15 schizophrenia-associated loci. The British journal of psychiatry: the journal of mental science. 2014; 204(2):108-14. doi: 10.1192/bjp.bp.113.131052. PubMed PMID: 24311552; PubMed Central PMCID: PMC3909838.

11. Rosenberg R E, Law J K, Yenokyan G, McGready J, Kaufmann W E, Law P A. Characteristics and concordance of autism spectrum disorders among 277 twin pairs. Archives of pediatrics & adolescent medicine. 2009; 163(10):907-14. doi: 10.1001/archpediatrics.2009.98. PubMed PMID: 19805709.
12. Shlien A and Malkin D. Copy number variations and cancer. Genome Medicine. 2009; 1(6):62. doi: 10.1186/gm62. PMID: 19566914. PMCID: PMC2703871.
13. Stadler Z K, Esposito D, Shah S, Vijai J, Yamrom B, Levy D, Lee Y H, Kendall J, Leotta A, Ronemus M, Hansen N, Sarrel K, Rau-Murthy R, Schrader K, Kauff N, Klein R J, Lipkin S M, Murali R, Robson M, Sheinfeld J, Feldman D, Bosl G, Norton L, Wigler M, Offit K. Rare de novo germline copy-number variation in testicular cancer. American journal of human genetics. 2012; 91(2):379-83. doi: 10.1016/j.ajhg.2012.06.019. PubMed PMID: 22863192; PubMed Central PMCID: PMC3415553.
14. Sudmant P H, Kitzman J O, Antonacci F, Alkan C, Malig M, Tsalenko A, Sampas N, Bruhn L, Shendure J, Genomes P, Eichler E E. Diversity of human copy number variation and multicopy genes. Science. 2010; 330(6004): 641-6. doi: 10.1126/science.1197005. PubMed PMID: 21030649; PubMed Central PMCID: PMC3020103.
15. Szatkiewicz J P, O'Dushlaine C, Chen G, Chambert K, Moran J L, Neale B M, Fromer M, Ruderfer D, Akterin S, Bergen S E, Kahler A, Magnusson P K, Kim Y, Crowley J J, Rees E, Kirov G, O'Donovan M C, Owen M J, Walters J, Scolnick E, Sklar P, Purcell S, Hultman C M, McCarroll S A, Sullivan P F. Copy number variation in schizophrenia in Sweden. Molecular psychiatry. 2014; 19(7):762-73. doi: 10.1038/mp.2014.40. PubMed PMID: 24776740; PubMed Central PMCID: PMC4271733.
16. Warburton D, Ronemus M, Kline J, Jobanputra V, Williams I, Anyane-Yeboa K, Chung W, Yu L, Wong N, Awad D, Yu C Y, Leotta A, Kendall J, Yamrom B, Lee Y H, Wigler M, Levy D. The contribution of de novo and rare inherited copy number changes to congenital heart disease in an unselected sample of children with conotruncal defects or hypoplastic left heart disease. Human genetics. 2014; 133(1):11-27. doi: 10.1007/s00439-013-1353-9. PubMed PMID: 23979609; PubMed Central PMCID: PMC3880624.
17. Willyard C. Copy number variations' effect on drug response still overlooked. Nature medicine. 2015; 21(3): 206. doi: 10.1038/nm0315-206. PubMed PMID: 25742449.

What is claimed is:

1. A sequencing library composition comprising a first mixture of different chimeric genomic nucleic acid fragments, wherein the mixture of different chimeric genomic nucleic acid fragments contains at least 100,000 different fragments, wherein the chimeric genomic nucleic acid fragments are about 250 to less than about 1000 base pairs in length, wherein each different fragment in the mixture comprises randomly ligated DNA segments, wherein each DNA segment in the fragment is a nucleic acid molecule at least 27 base pairs in length resulting from random fragmentation of a single genome for which a reference genome is available, wherein at least 50% of the segments in the at least 100,000 different fragments are about 30 to 50 base pairs in length.

2. The composition of claim 1, enriched for chimeric genomic nucleic acid fragments about 400 to about 500 base pairs in length.

3. The composition of claim 1, further comprising a sequencing adaptor ligated to the termini of the chimeric genomic nucleic acid fragments.

4. The composition of claim 3, wherein the sequence adaptor ligated to the termini of the chimeric genomic nucleic acid fragments comprises a barcode identifying the genomic source of the fragment.

5. The composition of claim 4, wherein the sequence adaptor ligated to the termini of the chimeric genomic nucleic acid fragments comprises primer binding site for amplification.

6. The composition of claim 1, wherein the genomic nucleic acids are extracted from a cell, a tissue, a tumor, a cell line or from blood.

7. The composition of claim 1, comprising a collection of multiple mixtures of different chimeric genomic nucleic acid fragments, wherein each mixture of fragments in the collection is obtained from a different genome than any other mixture in the collection.

8. The composition of claim 7, wherein each mixture of chimeric genomic nucleic acid fragments contains fragments having a sequencing adaptor containing a unique barcode ligated onto only fragments within the mixture, such that the collection of mixtures can be multiplexed.

9. A process for obtaining genomic copy number information from a genome, comprising
　i) obtaining the nucleic acid sequence of the different chimeric genomic nucleic acid fragments of the composition of claim 6;
　ii) identifying and mapping to a genome each Maximal Almost-unique Match (MAM) within a sequenced chimeric genomic nucleic acid fragment; and
　iii) counting the number of mapped MAMs within a binned genome,
　thereby obtaining genomic copy number information.

10. The composition of claim 1, wherein the mixture of chimeric genomic nucleic acid fragments contain ligated segments whose two ligation points form a sequence other than a restriction enzyme recognition site.

11. The composition of claim 1, wherein the segments are ligated directly to each other to form a fragment.

12. The composition of claim 1, wherein the random fragmentation of a single genome comprises mechanical shearing or enzymatic fragmentation by (a) generating random DNA nicks in the genome, and (b) cutting the DNA strand opposite the nick, thereby producing dsDNA breaks in the genomic nucleic acid; and the randomly ligated DNA segments are randomly blunt-end ligated DNA segments.

13. The composition of claim 1, wherein the segments in each of the at least 100,000 different fragments map to regions of the reference genome 10,000 or more base pairs apart.

* * * * *